(12) United States Patent
Ji et al.

(10) Patent No.: US 11,742,519 B2
(45) Date of Patent: Aug. 29, 2023

(54) SILICON-BASED ENERGY STORAGE DEVICES WITH ELECTROLYTE ADDITIVE COMPOUNDS

(71) Applicant: Enevate Corporation, Irvine, CA (US)

(72) Inventors: Liwen Ji, San Diego, CA (US); Benjamin Yong Park, Mission Viejo, CA (US)

(73) Assignee: Enevate Corporation, Irvine, CA (US)

( * ) Notice: Subject to any disclaimer, the term of this patent is extended or adjusted under 35 U.S.C. 154(b) by 342 days.

(21) Appl. No.: 16/890,499

(22) Filed: Jun. 2, 2020

(65) Prior Publication Data

US 2020/0388880 A1 Dec. 10, 2020

Related U.S. Application Data

(60) Provisional application No. 62/857,768, filed on Jun. 5, 2019.

(51) Int. Cl.
| | |
|---|---|
| *H01M 10/0567* | (2010.01) |
| *H01M 4/38* | (2006.01) |
| *H01M 4/04* | (2006.01) |
| *H01M 4/36* | (2006.01) |
| *H01M 4/587* | (2010.01) |

(Continued)

(52) U.S. Cl.
CPC ......... *H01M 10/0567* (2013.01); *C07C 69/02* (2013.01); *C07C 69/36* (2013.01); *C07C 69/96* (2013.01); *C07D 317/04* (2013.01); *C07D 319/12* (2013.01); *C07D 321/00* (2013.01); *H01M 4/0404* (2013.01); *H01M 4/364* (2013.01); *H01M 4/386* (2013.01); *H01M 4/587* (2013.01); *H01M 10/0525* (2013.01); *H01M 2300/0025* (2013.01)

(58) Field of Classification Search
CPC ........... H01M 10/0567; H01M 4/0404; H01M 4/364; H01M 4/386; H01M 4/587; H01M 10/0525; H01M 2300/0025; H01M 4/1395
See application file for complete search history.

(56) References Cited

U.S. PATENT DOCUMENTS

| | | | | | |
|---|---|---|---|---|---|
| 2009/0325065 | A1* | 12/2009 | Fujii | ................. | H01M 10/0569 429/207 |
| 2012/0129054 | A1* | 5/2012 | Huang | .............. | H01M 10/0567 429/342 |

(Continued)

OTHER PUBLICATIONS

M. D. Levi, et al., J. Electrochem. Soc. 2004, 151 (6), A848-A856.

(Continued)

*Primary Examiner* — Stewart A Fraser
(74) *Attorney, Agent, or Firm* — McAndrews, Held & Malloy, Ltd.

(57) ABSTRACT

Electrolytes and electrolyte additives for energy storage devices are disclosed. The energy storage device comprises a first electrode and a second electrode, where one or both of the first electrode and the second electrode is a Si-based electrode, a separator between the first electrode and the second electrode, an electrolyte, and at least one electrolyte additive compound selected from a carbonate, oxalate, trioxidane, peroxide, peroxoate, dioxetanone, oxepane dione, oxetane dione, anhydride, oxalate or 1,4-dioxane-2,3-dione; each of which may be optionally substituted.

15 Claims, 31 Drawing Sheets

(51) Int. Cl.
*H01M 10/0525* (2010.01)
*C07D 317/04* (2006.01)
*C07D 319/12* (2006.01)
*C07D 321/00* (2006.01)
*C07C 69/36* (2006.01)
*C07C 69/02* (2006.01)
*C07C 69/96* (2006.01)

(56) References Cited

U.S. PATENT DOCUMENTS

| | | | | |
|---|---|---|---|---|
| 2014/0302399 | A1* | 10/2014 | Saimen | H01M 10/0565 429/308 |
| 2016/0126591 | A1* | 5/2016 | Zhang | H01M 6/14 429/303 |
| 2021/0202992 | A1* | 7/2021 | Mendez Agudelo | H01G 11/62 |

OTHER PUBLICATIONS

F. Coowar, et al., J. Power Sources. 1998, 75, 144-150.
L. J. Krause, et al., J. Electrochem. Soc. 2017, 164, A2527-A2533.
M. C. Smart, et al., JPL Technical Report. 1992.

* cited by examiner

SILICON-BASED ENERGY STORAGE DEVICES WITH ELECTROLYTE ADDITIVE COMPOUNDS

CROSS-REFERENCE TO RELATED APPLICATIONS

This application claims the benefit of U.S. Provisional Application No. 62/857,768, filed Jun. 5, 2019. The entirety of each of the above referenced applications is hereby incorporated by reference.

FIELD

The present application relates generally to electrolytes for energy storage devices such as batteries. In particular, the present application relates to electrolytes and additives for use in lithium-ion energy storage devices with silicon-based anode materials.

BACKGROUND

Conventional approaches for battery electrolytes may be costly, cumbersome, and/or inefficient—e.g., they may be complex and/or time consuming to implement, and may limit battery lifetime.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

In some aspects, energy storage devices such as batteries are provided. In some embodiments, the energy storage device includes a first electrode and a second electrode, wherein at least one of the first electrode and the second electrode is a Si-based electrode. In some embodiments, the energy storage device includes a separator between the first electrode and the second electrode. In some embodiments, the energy storage device includes an electrolyte. In some embodiments, the energy storage device includes at least one electrolyte additive compound.

In some embodiments, the second electrode is a Si-dominant electrode. In some embodiments, the second electrode comprises a self-supporting composite material film. In some embodiments, the composite material film comprises greater than 0% and less than about 90% by weight of silicon particles, and greater than 0% and less than about 90% by weight of one or more types of carbon phases, wherein at least one of the one or more types of carbon phases is a substantially continuous phase that holds the composite material film together such that the silicon particles are distributed throughout the composite material film.

In some embodiments, the electrolyte further comprises fluoroethylene carbonate (FEC). In some embodiments, the electrolyte is substantially free of non-fluorine containing cyclic carbonate.

DETAILED DESCRIPTION

Figure 1:
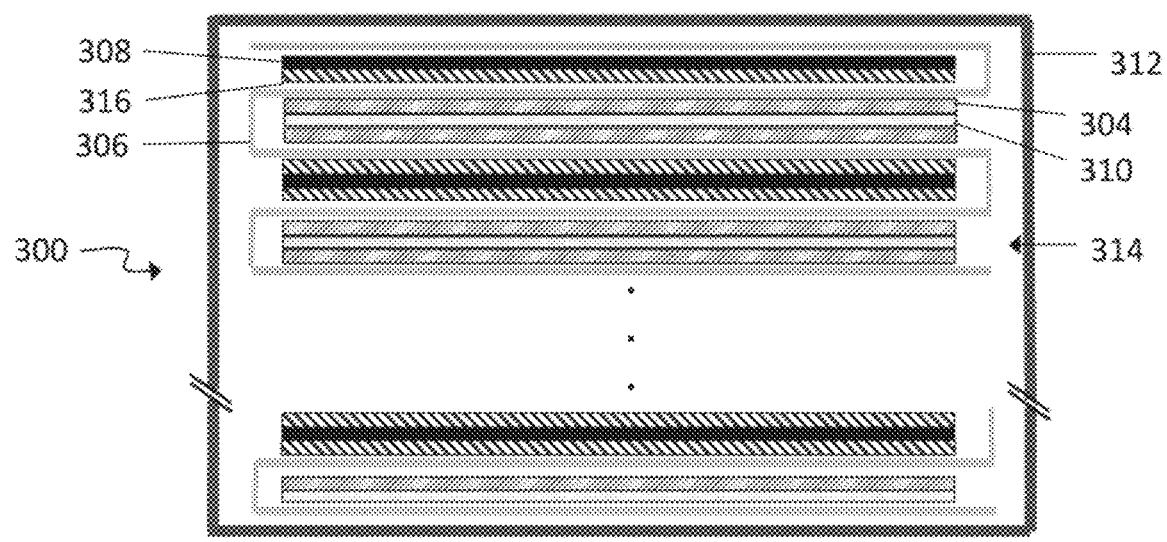
FIG. 1 is a cross-sectional schematic diagram of an example of a lithium ion battery, in accordance with an example embodiment of the disclosure.

As the demands for both zero-emission electric vehicles and grid-based energy storage systems increase, lower costs and improvements in energy density, power density, and safety of lithium (Li)-ion batteries are highly desirable. Enabling the high energy density and safety of Li-ion batteries requires the development of high-capacity, and high-voltage cathodes, high-capacity anodes and accordingly functional electrolytes with high voltage stability, interfacial compatibility with electrodes and safety.

A lithium-ion battery typically includes a separator and/or electrolyte between an anode and a cathode. In one class of batteries, the separator, cathode and anode materials are individually formed into sheets or films. Sheets of the cathode, separator and anode are subsequently stacked or rolled with the separator separating the cathode and anode (e.g., electrodes) to form the battery. Typical electrodes include electro-chemically active material layers on electrically conductive metals (e.g., aluminum and copper). Films can be rolled or cut into pieces which are then layered into stacks. The stacks are of alternating electro-chemically active materials with the separator between them.

Si is one of the most promising anode materials for Li-ion batteries due to its high specific gravimetric and volumetric capacity (3579 mAh/g and 2194 mAh/cm$^3$ vs. 372 mAh/g and 719 mAh/cm$^3$ for graphite), and low lithiation potential (<0.4 V vs. Li/Li+). Among the various cathodes presently available, layered lithium transition-metal oxides such as Ni-rich Li[Ni$_x$Co$_y$Mn(Al)$_{1-x-y}$]O$_2$ (NCM or NCA) are the most promising ones due to their high theoretical capacity (~280 mAh/g) and relatively high average operating potential (3.6 V vs Li/Li+). In addition to Ni-rich NCM or NCA cathode, LiCoO$_2$ (LCO) is also a very attractive cathode material because of its relatively high theoretical specific capacity of 274 mAh g$^{-1}$, high theoretical volumetric capacity of 1363 mAh cm$^{-3}$, low self-discharge, high discharge voltage, and good cycling performance. Coupling Si anodes with high-voltage Ni-rich NCM (or NCA) or LCO cathodes can deliver more energy than conventional Li-ion batteries with graphite-based anodes, due to the high capacity of these new electrodes. However, both Si-based anodes and high-voltage Ni rich NCM (or NCA) or LCO cathodes face formidable technological challenges, and long-term cycling stability with high-Si anodes paired with NCM or NCA cathodes has yet to be achieved.

For anodes, silicon-based materials can provide significant improvement in energy density. However, the large volumetric expansion (>300%) during the Li alloying/dealloying processes can lead to disintegration of the active material and the loss of electrical conduction paths, thereby reducing the cycling life of the battery. In addition, an unstable solid electrolyte interphase (SEI) layer can develop on the surface of the cycled anodes, and leads to an endless exposure of Si particle surfaces to the liquid electrolyte. This results in an irreversible capacity loss at each cycle due to the reduction at the low potential where the liquid electrolyte reacts with the exposed surface of the Si anode. In addition, oxidative instability of the conventional non-aqueous electrolyte takes place at voltages beyond 4.5 V, which can lead to accelerated decay of cycling performance. Because of the generally inferior cycle life of Si compared to graphite, only a small amount of Si or Si alloy is used in conventional anode materials.

The NCM (or NCA) or LCO cathode usually suffers from an inferior stability and a low capacity retention at a high cut-off potential. The reasons can be ascribed to the unstable surface layer's gradual exfoliation, the continuous electrolyte decomposition, and the transition metal ion dissolution into electrolyte solution. The major limitations for LCO cathode are high cost, low thermal stability, and fast capacity fade at high current rates or during deep cycling. LCO cathodes are expensive because of the high cost of Co. Low thermal stability refers to exothermic release of oxygen when a lithium metal oxide cathode is heated. In order to make good use of Si anode//NCM or NCA cathode-, and Si anode//LCO cathode-based Li-ion battery systems, the aforementioned barriers need to be overcome.

One strategy for overcoming these barriers includes exploring new electrolyte additives in order to make good use of Si anode//NCM or NCA cathode-, and Si anode//LCO cathode-based full cells. The next generation of electrolyte additives to be developed should be able to form a uniform, stable SEI layer on the surface of Si anodes. This layer should have low impedance and be electronically insulating, but ionically conductive to Li-ion. Additionally, the SEI layer formed by the additive should have excellent elasticity and mechanical strength to overcome the problem of expansion and shrinkage of the Si anode volume. On the cathode side, the ideal additives should be oxidized preferentially to the solvent molecule in the bare electrolyte, resulting in a protective cathode electrolyte interphase (CEI) film formed on the surface of the Ni-rich NCM (or NCA) and LCO cathodes. At the same time, it should help alleviate the dissolution phenomenon of transition metal ions and decrease surface resistance on cathode side. In addition, they could help improve the physical properties of the electrolyte such as ionic conductivity, viscosity, and wettability.

The term "alkyl" refers to a straight or branched, saturated, aliphatic radical having the number of carbon atoms indicated. The alkyl moiety may be branched or straight chain. For example, C1-C6 alkyl includes, but is not limited to, methyl, ethyl, propyl, isopropyl, butyl, isobutyl, sec-butyl, tert-butyl, pentyl, isopentyl, hexyl, etc. Other alkyl groups include, but are not limited to heptyl, octyl, nonyl, decyl, etc. Alkyl can include any number of carbons, such as 1-2, 1-3, 1-4, 1-5, 1-6, 1-7, 1-8, 1-9, 1-10, 1-11, 1-12 2-3, 2-4, 2-5, 2-6, 3-4, 3-5, 3-6, 4-5, 4-6 and 5-6. The alkyl group is typically monovalent, but can be divalent, such as when the alkyl group links two moieties together.

The term "fluoro-alkyl" refers to an alkyl group where one, some, or all hydrogen atoms have been replaced by fluorine.

The term "alkylene" refers to an alkyl group, as defined above, linking at least two other groups, i.e., a divalent hydrocarbon radical. The two moieties linked to the alkylene can be linked to the same atom or different atoms of the alkylene. For instance, a straight chain alkylene can be the bivalent radical of —(CH$_2$)$_n$—, where n is 1, 2, 3, 4, 5, 6, 7, 8, 9, or 10. Alkylene groups include, but are not limited to, methylene, ethylene, propylene, isopropylene, butylene, isobutylene, sec-butylene, pentylene and hexylene.

The term "alkoxy" refers to alkyl group having an oxygen atom that either connects the alkoxy group to the point of attachment or is linked to two carbons of the alkoxy group. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. For example, the alkoxy groups can be substituted with halogens to form a "halo-alkoxy" group, or substituted with fluorine to form a "fluoro-alkoxy" group.

The term "alkenyl" refers to either a straight chain or branched hydrocarbon of 2 to 6 carbon atoms, having at least one double bond. Examples of alkenyl groups include, but are not limited to, vinyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can also have from 2 to 3, 2 to 4, 2 to 5, 3 to 4, 3 to 5, 3 to 6, 4 to 5, 4 to 6 and 5 to 6 carbons. The alkenyl group is typically monovalent, but can be divalent, such as when the alkenyl group links two moieties together.

The term "alkenylene" refers to an alkenyl group, as defined above, linking at least two other groups, i.e., a divalent hydrocarbon radical. The two moieties linked to the alkenylene can be linked to the same atom or different atoms of the alkenylene. Alkenylene groups include, but are not limited to, ethenylene, propenylene, isopropenylene, butenylene, isobutenylene, sec-butenylene, pentenylene and hexenylene.

The term "alkynyl" refers to either a straight chain or branched hydrocarbon of 2 to 6 carbon atoms, having at least one triple bond. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can also have from 2 to 3, 2 to 4, 2 to 5, 3 to 4, 3 to 5, 3 to 6, 4 to 5, 4 to 6 and 5 to 6 carbons. The alkynyl group is typically monovalent, but can be divalent, such as when the alkynyl group links two moieties together.

The term "alkynylene" refers to an alkynyl group, as defined above, linking at least two other groups, i.e., a divalent hydrocarbon radical. The two moieties linked to the alkynylene can be linked to the same atom or different atoms of the alkynylene. Alkynylene groups include, but are not limited to, ethynylene, propynylene, butynylene, sec-butynylene, pentynylene and hexynylene.

The term "cycloalkyl" refers to a saturated or partially unsaturated, monocyclic, fused bicyclic, bridged polycyclic, or spiro ring assembly containing from 3 to 12, from 3 to 10, or from 3 to 7 ring atoms, or the number of atoms indicated. Monocyclic rings include, for example, cyclopropyl, cyclobutyl, cyclopentyl, cyclohexyl, and cyclooctyl. Bicyclic and polycyclic rings include, for example, norbornane, decahydronaphthalene and adamantane. For example, C3-C8 cycloalkyl includes cyclopropyl, cyclobutyl, cyclopentyl, cyclohexyl, cyclooctyl, and norbornane. As used herein, the term "fused" refers to two rings which have two atoms and one bond in common. For example, in the following structure, rings A and B are fused

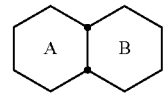

As used herein, the term "bridged polycyclic" refers to compounds wherein the cycloalkyl contains a linkage of one or more atoms connecting non-adjacent atoms. The following structures

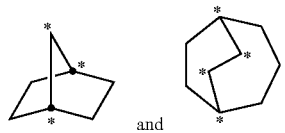 [SMILES: C1C[C@H]2CC[C@H]1C2 ; C1CC2CCC(C1)CC2]

and are examples of "bridged" rings. As used herein, the term "spiro" refers to two rings which have one atom in common and the two rings are not linked by a bridge. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl, and norbornanyl; and examples of spiro cycloalkyl groups include spiro[3.3]heptane and spiro[4.5]decane.

The term "cycloalkylene" refers to a cycloalkyl group, as defined above, linking at least two other groups, i.e., a divalent hydrocarbon radical. The two moieties linked to the cycloalkylene can be linked to the same atom or different atoms of the cycloalkylene. Cycloalkylene groups include, but are not limited to, cyclopropylene, cyclobutylene, cyclopentylene, cyclohexylene, and cyclooctylene.

The term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. Aryl groups may include fused multicyclic ring assemblies wherein only one ring in the multicyclic ring assembly is aromatic. Aryl groups can be mono-, di- or tri-substituted by one, two or three radicals. Preferred as aryl is naphthyl, phenyl or phenyl mono- or disubstituted by alkoxy, phenyl, halogen, alkyl or trifluoromethyl, especially phenyl or phenyl-mono- or disubstituted by alkoxy, halogen or trifluoromethyl, and in particular phenyl.

The term "arylene" refers to an aryl group, as defined above, linking at least two other groups. The two moieties linked to the arylene are linked to different atoms of the arylene. Arylene groups include, but are not limited to, phenylene.

The term "heteroaryl" refers to a monocyclic or fused bicyclic or tricyclic aromatic ring assembly containing 5 to 16 ring atoms, where from 1 to 4 of the ring atoms are a heteroatom each N, O or S. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred 4-thiazolyl. Triazolyl is preferably 1-, 2- or 5-(1,2,4-triazolyl). Tetrazolyl is preferably 5-tetrazolyl.

Preferably, heteroaryl is pyridyl, indolyl, quinolinyl, pyrrolyl, thiazolyl, isoxazolyl, triazolyl, tetrazolyl, pyrazolyl, imidazolyl, thienyl, furanyl, benzothiazolyl, benzofuranyl, isoquinolinyl, benzothienyl, oxazolyl, indazolyl, or any of the radicals substituted, especially mono- or di-substituted.

The term "heteroalkyl" refers to an alkyl group having from 1 to 3 heteroatoms such as N, O and S. The heteroatoms can also be oxidized, such as, but not limited to, —S(O)— and —S(O)$_2$—. For example, heteroalkyl can include ethers, thioethers, alkyl-amines and alkyl-thiols.

The term "heteroalkylene" refers to a heteroalkyl group, as defined above, linking at least two other groups. The two moieties linked to the heteroalkylene can be linked to the same atom or different atoms of the heteroalkylene.

The term "heterocycloalkyl" refers to a ring system having from 3 ring members to about 20 ring members and from 1 to about 5 heteroatoms such as N, O and S. The heteroatoms can also be oxidized, such as, but not limited to, —S(O)— and —S(O)$_2$—. For example, heterocycle includes, but is not limited to, tetrahydrofuranyl, tetrahydrothiophenyl, morpholino, pyrrolidinyl, pyrrolinyl, imidazolidinyl, imidazolinyl, pyrazolidinyl, pyrazolinyl, piperazinyl, piperidinyl, indolinyl, quinuclidinyl and 1,4-dioxa-8-aza-spiro[4.5]dec-8-yl.

The term "heterocycloalkylene" refers to a heterocyclalkyl group, as defined above, linking at least two other groups. The two moieties linked to the heterocycloalkylene can be linked to the same atom or different atoms of the heterocycloalkylene.

The term "optionally substituted" is used herein to indicate a moiety that can be unsubstituted or substituted by one or more substituent. When a moiety term is used without specifically indicating as substituted, the moiety is unsubstituted.

To overcome the current obstacles associated with developing high-energy full-cells with Si-based anodes, the next generation of oxidation-stable electrolytes or electrolyte additives are developed. The electrolyte or electrolyte additives can form a stable, electronically insulating but ionically conducting SEI layer on the surface of Si anodes. Additionally, these electrolytes or additives may also help modify cathode surfaces, forming stable CEI layers. These could enable the electrochemical stability of Li-ion batteries when cycled at higher voltages and help with calendar life of the batteries. In addition, to alleviate battery safety concerns, these additives may impart an increased thermal stability to the organic components of the electrolyte, drive a rise in the flash point of the electrolyte formulations, increase the flame-retardant effectiveness and enhance thermal stability of SEI or CEI layers on the surface of electrodes.

In the present disclosure, the use of functional chemical compounds comprising a carbonate, oxalate, trioxidane, peroxide, peroxoate, dioxetanone, oxepane dione, oxetane dione, anhydride, oxalate or 1,4-dioxane-2,3-dione, which may be optionally substituted, as an electrolyte additive for energy storage devices with Si-dominant anodes is described. Due to their unique chemical structures and functional groups, inclusion of these electrolyte additives may bring the following benefits: (i) stabilize solid/electrolyte interface film to reduce electrolyte reactions (oxidation on the NCM, NCA, or LCO cathode and reduction on the Si anode), prevent Si anode volume expansion, and protect transition metal ion dissolution from NCM or NCA cathode and stabilize the subsequent structure changes; and avoid the exothermic reaction between the released oxygen for LCO and organic electrolyte and enhance the thermal stability of LCO cathode; and (ii) reduce the flammability and enhance the thermal stability of organic electrolytes and increase the safety of electrolyte solutions. Due to their versatility in reaction chemistry and overall stability in electrochemical environments, as well as having excellent flame resistance or fire retardant properties, involving a carbonate, oxalate, trioxidane, peroxide, peroxoate, dioxetanone, oxepane dione, oxetane dione, anhydride, oxalate or 1,4-dioxane-2,3-dione, which may be optionally substituted, as electrolyte additives into electrolyte solutions may help improve both overall electrochemical performance and safety of Si anode-based Li-ion batteries.

Typical carbon anode electrodes include a current collector such as a copper sheet. Carbon is deposited onto the collector along with an inactive binder material. Carbon is often used because it has excellent electrochemical properties and is also electrically conductive. If the current collector layer (e.g., copper layer) was removed, the carbon would likely be unable to mechanically support itself. Therefore, conventional electrodes require a support structure such as the collector to be able to function as an electrode. The electrode (e.g., anode or cathode) compositions described in this application can produce electrodes that are self-supported. The need for a metal foil current collector is eliminated or minimized because conductive carbonized polymer is used for current collection in the anode structure as well as for mechanical support. In typical applications for the mobile industry, a metal current collector is typically added to ensure sufficient rate performance. The carbonized polymer can form a substantially continuous conductive carbon phase in the entire electrode as opposed to particulate carbon suspended in a non-conductive binder in one class of conventional lithium-ion battery electrodes. Advantages of a carbon composite blend that utilizes a carbonized polymer can include, for example, 1) higher capacity, 2) enhanced overcharge/discharge protection, 3) lower irreversible capacity due to the elimination (or minimization) of metal foil current collectors, and 4) potential cost savings due to simpler manufacturing.

Anode electrodes currently used in the rechargeable lithium-ion cells typically have a specific capacity of approximately 200 milliamp hours per gram (including the metal foil current collector, conductive additives, and binder material). Graphite, the active material used in most lithium ion battery anodes, has a theoretical energy density of 372 milliamp hours per gram (mAh/g). In comparison, silicon has a high theoretical capacity of 4200 mAh/g. In order to increase volumetric and gravimetric energy density of lithium-ion batteries, silicon may be used as the active material for the cathode or anode. Several types of silicon materials, e.g., silicon nanopowders, silicon nanofibers, porous silicon, and ball-milled silicon, have also been reported as viable candidates as active materials for the negative or positive electrodes. Small particle sizes (for example, sizes in the nanometer range) generally can increase cycle life performance. They also can display very high initial irreversible capacity. However, small particle sizes also can result in very low volumetric energy density (for example, for the overall cell stack) due to the difficulty of packing the active material. Larger particle sizes, (for example, sizes in the micron range) generally can result in higher density anode material. However, the expansion of the silicon active material can result in poor cycle life due to particle cracking. For example, silicon can swell in excess of 300% upon lithium insertion. Because of this expansion, anodes including silicon should be allowed to expand while maintaining electrical contact between the silicon particles.

Cathode electrodes described herein may include metal oxide cathode materials, such as Lithium Cobalt Oxide ($LiCoO_2$) (LCO), Ni-rich oxides, high voltage cathode materials, lithium-rich oxides, nickel-rich layered oxides, lithium rich layered oxides, high-voltage spinel oxides, and high-voltage polyanionic compounds. Ni-rich oxides and/or high voltage cathode materials may include NCM and NCA. One example of a NCM material includes $LiNi_{0.6}Co_{0.2}Mn_{0.2}O_2$ (NCM-622). Lithium rich oxides may include $xLi_2Mn_3O_2 \cdot (1-x)LiNi_aCo_bMn_cO_2$. Nickel-rich layered oxides may include $LiNi_{1+x}M_{1-x}O_z$ (where M=Co, Mn or Al). Lithium rich layered oxides may include $LiNi_{1+x}M_{1-x}O_2$ (where M=Co, Mn or Ni). High-voltage spinel oxides may include $LiNi_{0.5}Mn_{1.5}O_4$. High-voltage polyanionic compounds may include phosphates, sulfates, silicates, etc.

As described herein and in U.S. patent application Ser. Nos. 13/008,800 and 13/601,976, entitled "Composite Materials for Electrochemical Storage" and "Silicon Particles for Battery Electrodes," respectively, certain embodiments utilize a method of creating monolithic, self-supported anodes using a carbonized polymer. Because the polymer is converted into an electrically conductive and electrochemically active matrix, the resulting electrode is conductive enough that, in some embodiments, a metal foil or mesh current collector can be omitted or minimized. The converted polymer also acts as an expansion buffer for silicon particles during cycling so that a high cycle life can be achieved. In certain embodiments, the resulting electrode is an electrode that is comprised substantially of active material. In further embodiments, the resulting electrode is substantially active material. The electrodes can have a high energy density of between about 500 mAh/g to about 1200 mAh/g that can be due to, for example, 1) the use of silicon, 2) elimination or substantial reduction of metal current collectors, and 3) being comprised entirely or substantially entirely of active material.

As described herein and in U.S. patent application Ser. No. 14/800,380, entitled "Electrolyte Compositions for Batteries," the entirety of which is hereby incorporated by reference, composite materials can be used as an anode in most conventional Li-ion batteries; they may also be used as the cathode in some electrochemical couples with additional additives. The composite materials can also be used in either secondary batteries (e.g., rechargeable) or primary batteries (e.g., non-rechargeable). In some embodiments, the composite materials can be used in batteries implemented as a pouch cell, as described in further details herein. In certain embodiments, the composite materials are self-supported structures. In further embodiments, the composite materials are self-supported monolithic structures. For example, a collector may be included in the electrode comprised of the composite material. In certain embodiments, the composite material can be used to form carbon structures discussed in U.S. patent application Ser. No. 12/838,368 entitled "Carbon Electrode Structures for Batteries," the entirety of which is hereby incorporated by reference. Furthermore, the composite materials described herein can be, for example, silicon composite materials, carbon composite materials, and/or silicon-carbon composite materials.

In some embodiments, a largest dimension of the silicon particles can be less than about 40 μm, less than about 1 μm, between about 10 nm and about 40 μm, between about 10 nm and about 1 μm, less than about 500 nm, less than about 100 nm, and about 100 nm. All, substantially all, or at least some of the silicon particles may comprise the largest dimension described above. For example, an average or median largest dimension of the silicon particles can be less than about 40 μm, less than about 1 μm, between about 10 nm and about 40 μm, between about 10 nm and about 1 μm, less than about 500 nm, less than about 100 nm, and about 100 nm. The amount of silicon in the composite material can be greater than zero percent by weight of the mixture and composite material. In certain embodiments, the mixture comprises an amount of silicon, the amount being within a range of from about 0% to about 90% by weight, including from about 30% to about 80% by weight of the mixture. The amount of silicon in the composite material can be within a range of from about 0% to about 35% by weight, including from about 0% to about 25% by weight, from about 10% to about 35% by weight, and about 20% by weight. In further certain embodiments, the amount of silicon in the mixture is at least about 30% by weight. Additional embodiments of the amount of silicon in the composite material include more than about 50% by weight, between about 30% and about 80% by weight, between about 50% and about 70% by weight, and between about 60% and about 80% by weight. Furthermore, the silicon particles may or may not be pure silicon. For example, the silicon particles may be substantially silicon or may be a silicon alloy. In one embodiment, the silicon alloy includes silicon as the primary constituent along with one or more other elements.

As described herein, micron-sized silicon particles can provide good volumetric and gravimetric energy density combined with good cycle life. In certain embodiments, to obtain the benefits of both micron-sized silicon particles (e.g., high energy density) and nanometer-sized silicon particles (e.g., good cycle behavior), silicon particles can have an average particle size in the micron range and a surface including nanometer-sized features. In some embodiments, the silicon particles have an average particle size (e.g., average diameter or average largest dimension) between about 0.1 μm and about 30 μm or between about 0.1 μm and all values up to about 30 μm. For example, the silicon particles can have an average particle size between about 0.5 μm and about 25 μm, between about 0.5 μm and about 20 μm, between about 0.5 μm and about 15 μm, between about 0.5 µm and about 10 µm, between about 0.5 µm and about 5 µm, between about 0.5 µm and about 2 µm, between about 1 µm and about 20 µm, between about 1 µm and about 15 µm, between about 1 µm and about 10 µm, between about 5 µm and about 20 µm, etc. Thus, the average particle size can be any value between about 0.1 µm and about 30 µm, e.g., 0.1 µm, 0.5 µm, 1 µm, 5 µm, 10 µm, 15 µm, 20 µm, 25 µm, and 30 µm.

The composite material can be formed by pyrolyzing a polymer precursor, such as polyamide acid. The amount of carbon obtained from the precursor can be about 50 weight percent by weight of the composite material. In certain embodiments, the amount of carbon from the precursor in the composite material is about 10% to about 25% by weight. The carbon from the precursor can be hard carbon. Hard carbon can be a carbon that does not convert into graphite even with heating in excess of 2800 degrees Celsius. Precursors that melt or flow during pyrolysis convert into soft carbons and/or graphite with sufficient temperature and/or pressure. Hard carbon may be selected since soft carbon precursors may flow and soft carbons and graphite are mechanically weaker than hard carbons. Other possible hard carbon precursors can include phenolic resins, epoxy resins, and other polymers that have a very high melting point or are crosslinked. In some embodiments, the amount of hard carbon in the composite material has a value within a range of from about 10% to about 25% by weight, about 20% by weight, or more than about 50% by weight. In certain embodiments, the hard carbon phase is substantially amorphous. In other embodiments, the hard carbon phase is substantially crystalline. In further embodiments, the hard carbon phase includes amorphous and crystalline carbon. The hard carbon phase can be a matrix phase in the composite material. The hard carbon can also be embedded in the pores of the additives including silicon. The hard carbon may react with some of the additives to create some materials at interfaces. For example, there may be a silicon carbide layer between silicon particles and the hard carbon.

In certain embodiments, graphite particles are added to the mixture. Advantageously, graphite can be an electrochemically active material in the battery as well as an elastic deformable material that can respond to volume change of the silicon particles. Graphite is the preferred active anode material for certain classes of lithium-ion batteries currently on the market because it has a low irreversible capacity. Additionally, graphite is softer than hard carbon and can better absorb the volume expansion of silicon additives. In certain embodiments, a largest dimension of the graphite particles is between about 0.5 microns and about 20 microns. All, substantially all, or at least some of the graphite particles may comprise the largest dimension described herein. In further embodiments, an average or median largest dimension of the graphite particles is between about 0.5 microns and about 20 microns. In certain embodiments, the mixture includes greater than 0% and less than about 80% by weight of graphite particles. In further embodiments, the composite material includes about 40% to about 75% by weight graphite particles.

In certain embodiments, conductive particles which may also be electrochemically active are added to the mixture. Such particles can enable both a more electronically conductive composite as well as a more mechanically deformable composite capable of absorbing the large volumetric change incurred during lithiation and de-lithiation. In certain embodiments, a largest dimension of the conductive particles is between about 10 nanometers and about 7 millimeters. All, substantially all, or at least some of the conductive particles may comprise the largest dimension described herein. In further embodiments, an average or median largest dimension of the conductive particles is between about 10 nm and about 7 millimeters. In certain embodiments, the mixture includes greater than zero and up to about 80% by weight conductive particles. In further embodiments, the composite material includes about 45% to about 80% by weight conductive particles. The conductive particles can be conductive carbon including carbon blacks, carbon fibers, carbon nanofibers, carbon nanotubes, graphite, graphene, etc. Many carbons that are considered as conductive additives that are not electrochemically active become active once pyrolyzed in a polymer matrix. Alternatively, the conductive particles can be metals or alloys including copper, nickel, or stainless steel.

The composite material may also be formed into a powder. For example, the composite material can be ground into a powder. The composite material powder can be used as an active material for an electrode. For example, the composite material powder can be deposited on a collector in a manner similar to making a conventional electrode structure, as known in the industry.

In some embodiments, the full capacity of the composite material may not be utilized during use of the battery to improve battery life (e.g., number charge and discharge cycles before the battery fails or the performance of the battery decreases below a usability level). For example, a composite material with about 70% by weight silicon particles, about 20% by weight carbon from a precursor, and about 10% by weight graphite may have a maximum gravimetric capacity of about 2000 mAh/g, while the composite material may only be used up to a gravimetric capacity of about 550 to about 850 mAh/g. Although, the maximum gravimetric capacity of the composite material may not be utilized, using the composite material at a lower capacity can still achieve a higher capacity than certain lithium ion batteries. In certain embodiments, the composite material is used or only used at a gravimetric capacity below about 70% of the composite material's maximum gravimetric capacity. For example, the composite material is not used at a gravimetric capacity above about 70% of the composite material's maximum gravimetric capacity. In further embodiments, the composite material is used or only used at a gravimetric capacity below about 50% of the composite material's maximum gravimetric capacity or below about 30% of the composite material's maximum gravimetric capacity.

An electrolyte for a lithium ion battery can include a solvent and a lithium ion source, such as a lithium-containing salt. The composition of the electrolyte may be selected to provide a lithium ion battery with improved performance. In some embodiments, the electrolyte may contain an electrolyte additive. As described herein, a lithium ion battery may include a first electrode, a second electrode, a separator between the first electrode and the second electrode, and an electrolyte in contact with the first electrode, the second electrode, and the separator. The electrolyte serves to facilitate ionic transport between the first electrode and the second electrode. In some embodiments, the first electrode and the second electrode can refer to anode and cathode or cathode and anode, respectively.

In some embodiments, the electrolyte for a lithium ion battery may include a solvent comprising a fluorine-containing component, such as a fluorine-containing cyclic carbonate, a fluorine-containing linear carbonate, and/or a fluoroether. In some embodiments, the electrolyte can include more than one solvent. For example, the electrolyte may include two or more co-solvents. In some embodiments, at least one of the co-solvents in the electrolyte is a fluorine-containing compound. In some embodiments, the fluorine-containing compound may be fluoroethylene carbonate (FEC), or difluoroethylene carbonate (F2EC). In some embodiments, the co-solvent may be selected from the group consisting of FEC, ethyl methyl carbonate (EMC), 1,1,2,2-tetrafluoroethyl 2,2,3,3-tetrafluoropropyl ether, difluoroethylene carbonate (F2EC), ethylene carbonate (EC), diethyl carbonate (DEC), dimethyl carbonate (DMC), propylene carbonate (PC), Dimethoxy ethane (DME), and gamma-Butyrolactone (GBL). In some embodiments, the electrolyte contains FEC. In some embodiments, the electrolyte contains both EMC and FEC. In some embodiments, the electrolyte may further contain 1,1,2,2-tetrafluoroethyl 2,2,3,3-tetrafluoropropyl ether, EC, DEC, DMC, PC, GBL, and/or F2EC or some partially or fully fluorinated linear or cyclic carbonates, ethers, etc. as a co-solvent. In some embodiments, the electrolyte is free or substantially free of non-fluorine-containing cyclic carbonates, such as EC, GBL, and PC.

As used herein, a co-solvent of an electrolyte has a concentration of at least about 10% by volume (vol %). In some embodiments, a co-solvent of the electrolyte may be about 20 vol %, about 40 vol %, about 60 vol %, or about 80 vol %, or about 90 vol % of the electrolyte. In some embodiments, a co-solvent may have a concentration from about 10 vol % to about 90 vol %, from about 10 vol % to about 80 vol %, from about 10 vol % to about 60 vol %, from about 20 vol % to about 60 vol %, from about 20 vol % to about 50 vol %, from about 30 vol % to about 60 vol %, or from about 30 vol % to about 50 vol %.

For example, in some embodiments, the electrolyte may contain a fluorine-containing cyclic carbonate, such as FEC, at a concentration of about 10 vol % to about 60 vol %, including from about 20 vol % to about 50 vol %, and from about 20 vol % to about 40 vol %. In some embodiments, the electrolyte may comprise a linear carbonate that does not contain flourine, such as EMC, at a concentration of about 40 vol % to about 90 vol %, including from about 50 vol % to about 80 vol %, and from about 60 vol % to about 80 vol %. In some embodiments, the electrolyte may comprise 1,1,2,2-tetrafluoroethyl 2,2,3,3-tetrafluoropropyl ether at a concentration of from about 10 vol % to about 30 vol %, including from about 10 vol % to about 20 vol %.

In some embodiments, the electrolyte is substantially free of cyclic carbonates other than fluorine-containing cyclic carbonates (i.e., non-fluorine-containing cyclic carbonates). Examples of non-fluorine-containing carbonates include EC, PC, GBL, and vinylene carbonate (VC).

In some embodiments, the electrolyte may further comprise one or more additives. As used herein, an additive of the electrolyte refers to a component that makes up less than 10% by weight (wt %) of the electrolyte. In some embodiments, the amount of each additive in the electrolyte may be from about 0.2 wt % to about 1 wt %, 0.1 wt % to about 2 wt %, 0.2 wt % to about 9 wt %, from about 0.5 wt % to about 9 wt %, from about 1 wt % to about 9 wt %, from about 1 wt % to about 8 wt %, from about 1 wt % to about 8 wt %, from about 1 wt % to about 7 wt %, from about 1 wt % to about 6 wt %, from about 1 wt % to about 5 wt %, from about 2 wt % to about 5 wt %, or any value in between. In some embodiments, the total amount of the additive(s) may be from about 1 wt % to about 9 wt %, from about 1 wt % to about 8 wt %, from about 1 wt % to about 7 wt %, from about 2 wt % to about 7 wt %, or any value in between.

The electrolyte or additive may comprise functional compounds. In some embodiments, the electrolyte additive may be a carbonate, oxalate, trioxidane, peroxide, peroxoate, dioxetanone, oxepane dione, oxetane dione, anhydride, oxalate or 1,4-dioxane-2,3-dione, which may be optionally substituted. In some embodiments, the compound may be included in the electrolyte as a co-solvent. In other embodiments, the compound may be included in the electrolyte as an additive. For example, the electrolyte may contain a compound as a co-solvent at a concentration of about 10 vol % or more. In other embodiments, the electrolyte may contain a compound as an additive at less than 10 weight %.

Example general formulae of electrolyte additive compounds are shown below as (A)-(Q):

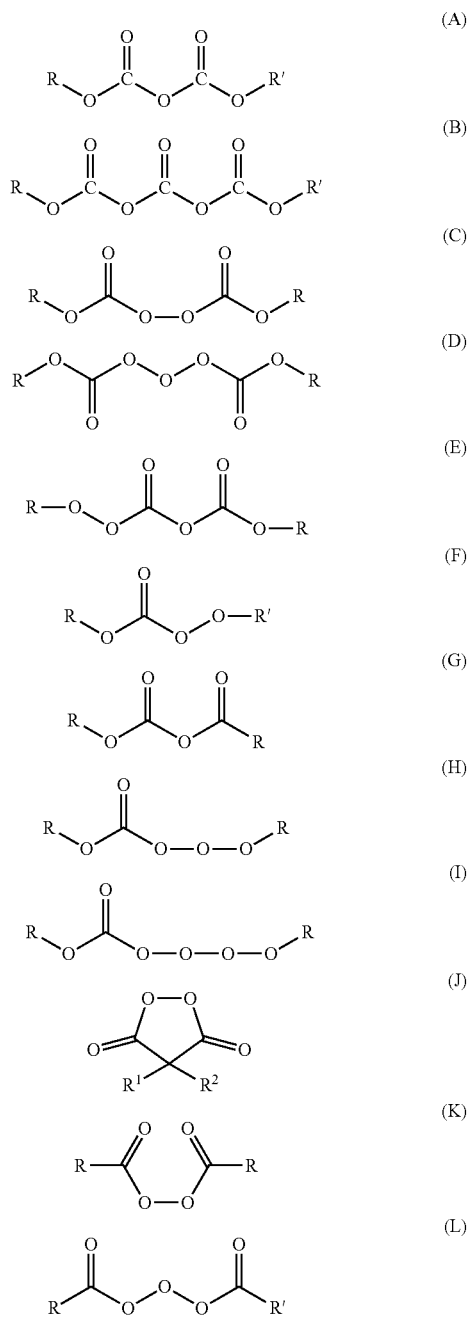

-continued

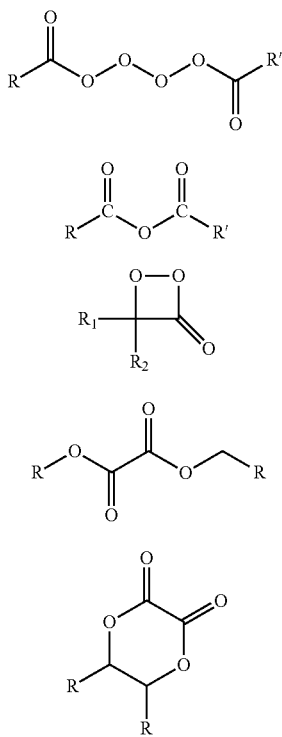

In some embodiments of the above example formulae (A)-(Q), each individual R, R', $R^1$ and $R^2$ group may be the same or different and may be selected from —H, —CN, an alkenyl, a heteroalkenyl, an alkynyl, a heteroalkynyl, an alkyl, —Si(CH$_3$)$_3$, a cycloalkyl and a heterocycloalkyl, which may be optionally substituted. In some embodiments, each individual R, R', $R^1$ and $R^2$ group may be the same or different and may be selected as above and may be further optionally substituted by —F, —CN, —CF$_3$ or a heterocycloalkyl.

In other embodiments, in the above formulae (A)-(Q), each individual R, R', $R^1$ and $R^2$ group may be the same or different and may be selected from the group consisting of H, alkyl, fluoro-alkyl, alkylene, alkoxy, alkenyl, alkenylene, alkynyl, alkynylene, cycloalkyl, cycloalkylene, aryl, arylene, heteroaryl, heteroalkyl, heteroalkylene, heterocycloalkyl, and heterocycloalkylene, as defined above, which may be further optionally substituted.

In some embodiments, the electrolyte additive compound is selected from Diallyl pyrocarbonate (DAPC), Di-tert-butyl dicarbonate (DTBDC), Di-Tert-butyl tricarbonate (DTBTC), dimethyl dicarbonate (CAS: 4525-33-1); diethyl pyrocarbonate (CAS: 1609-47-8); dipropyl dicarbonate (CAS: 43086-15-3); diisopropyl dicarbonate (CAS: 24425-00-1); dibutyl dicarbonate; (CAS: 4525-32-0); diisobutyl Dicarbonate; (CAS: 119174-41-3); Di-tert-butyl dicarbonate (CAS: 24424-99-5); Di-sec-butyl dicarbonate (CAS: 61114-48-5); Di-tert-amyl dicarbonate (CAS: 68835-89-2); dicyclohexyl dicarbonate (CAS: 61114-49-6); dibenzyl dicarbonate (CAS: 31139-36-3), dimethyl tricarbonate (CAS: 212077-60-6); formyl hydrogen tricarbonate, Dimethyl peroxydicarbonate (CAS: 15411-45-7); Diethyl peroxydicarbonate (CAS: 14666-78-5); Dipropyl peroxydicarbonate (CAS: 16066-38-9); butoxycarbonyloxy butyl carbonate (16215-49-9); Disisopropyl peroxydicarbonate (CAS: 105-64-6); Di-sec-butyl peroxydicarbonate (CAS: 19910-65-7); Isopropyl sec-butyl peroxydicarbonate (CAS: 78350-78-4); Di-tert-Bu-peroxydicarbonate; Dineopentylperoxydicarbonate (CAS: 86695-50-3); bis(2-ethylhexyl) peroxydicarbonate (CAS: 16111-62-9); isopropyl-sec-butylperoxydicarbonate (CAS: 78350-78-4); Dicyclohexyl peroxydicarbonate (CAS: 1561-49-5); Bis(tert-butylcyclohexyl) peroxydicarbonate (CAS: 15520-11-3); Bis(2-phenoxyethyl) peroxydicarbonate (CAS: 41935-39-1); Di-3-methyl-3-methoxybutyl peroxy dicarbonate (CAS: 75142-97-1); bis (3-methoxybutyl) peroxydicarbonate (CAS: 52238-68-3); disodium peroxydicarbonate (CAS: 3313-92-6); Dipotassium peroxydicarbonate (CAS: 589-97-9); Bis(trifluoromethyl)trioxidicarbonate, tert-Amylperoxy 2-ethylhexyl carbonate (CAS: 70833-40-8); tert-Butylperoxy isopropyl carbonate (CAS: 2372-21-6); Di-sec-butyl peroxycarbonate (CAS: 71501-14-9); tert-Butylperoxy 2-ethylhexyl carbonate (CAS: 34443-12-4), Allyl tert-butyl peroxycarbonate (CAS: 65700-08-5); bis[(4-tert-butylcyclohexyl)oxy] carbonate (CAS: 71331-99-2); Dicyclohexyl diperoxycarbonate (CAS: 2036-92-2); Trifluoro{[(trifluoromethoxy)carbonyl]peroxy}methane; 0-[2,2,2-trifluoro-1,1-bis(trifluoromethyl)ethyl]-0,0-(trifluoromethyl) peroxycarbonate (CAS: 55100-93-1); Sodium peroxocarbonate (CAS: 14455-47-1); Carbonofluoridoyl Trifluoromethoxy Carbonate; carbonofluoridoyloxy trifluoromethyl carbonate; Potassium peroxocarbonate, acetyl isopropyl carbonate (CAS: 60059-18-9); acetyl 1,2-dimethylpropyl carbonate (CAS: 76085-66-0), 2-Ethylhexyl 3-tert-butyltrioxidane-1-carboxylate; Carbonofluoridoylperoxy Trifluoromethyl Carbonate; Tert-butylperoxy 2-ethylhexylperoxy carbonate; Bis[(1-tert-butylcyclohexyl)peroxy] carbonate, 2-ethylhexyl (2-methylpropan-2-yl)oxyperoxy carbonate; 2-ethylhexyl 2-methylbutan-2-yloxyperoxy carbonate, cyclopropane malonyl peroxide; Cyclobutane malonyl peroxide (CAS: 34867-87-3); cyclopentane malonoyl peroxide; malonoyl peroxide; dimethylmalonyl peroxide; diethylmalonyl peroxide, acetyl butaneperoxoate (CAS: 13043-83-9); acetyl 2-methylbutyryl peroxide (CAS: 76085-60-4); acetyl 2,3-dimethylbutyryl peroxide (CAS: 76085-62-6); propanoyl butaneperoxoate (CAS: 13043-86-2); benzoyl peroxide (CAS: 94-36-0); acetyl benzoyl peroxide (CAS: 644-31-5); 1-O-acetyl 2-O-tert-butyl benzene-1,2-dicarboperoxoate; bis(trifluoroacetyl) peroxide (CAS: 383-73-3); acetyl cyclohexanesulfonyl peroxide (CAS: 3179-56-4); (2,2,2-trifluoroacetyl)oxy 2,2,2-trifluoroethaneperoxoate, (2,2,2-trifluoroacetyl)peroxy 2,2,2-trifluoroethaneperoxoate (CAS: 684-80-0), 1,2,3,4,6-pentaoxepane-5,7-dione, Acetic oxalic anhydride (CAS: 19037-85-5); 2-Ethoxy-2-oxoacetic anhydride (CAS: 119174-42-4); 1,2-Dioxetane-3,4-dione (CAS: 26974-08-3), 3,3-dimethyl-1,2-dioxetanone; 3-tert-butyl-1, 2-dioxetanone; spiro-cyclopentyl-1,2-dioxetanone; spiro-adamantyl-1,2-dioxetanone; firefly dioxetanone; Dimethyl oxalate (CAS: 553-90-2); Diethyl oxalate (CAS: 95-92-1); Dipropyl oxalate (CAS: 615-98-5); Diphenyl Oxalate (CAS: 3155-16-6); N,N'-Disuccinimidyl oxalate (CAS: 57296-03-4); diallyl oxalate (CAS: 615-99-6), 1,4-dioxane-2,3-dione; 5-methylidene-1,4-dioxane-2,3-dione; 5-ethenyl-1,4-dioxane-2,3-dione (CAS: 89543-86-2); 5-methyl-1,4-dioxane-2,3-dione (CAS: 89093-66-3); 5,6-dimethyl-1,4-dioxane-2, 3-dione (CAS: 89093-67-4); cis-5,6-diphenyl-1,4-dioxane-2,3-dione (CAS: 74888-53-2); bis(trifluoromethyl) dicarbonate; Dicarbamoyl dicarbonate, Trifluoromethoxycarbonyloxy trifluoromethyl carbonate, and diphenoyl peroxide.

Example structures of electrolyte additive compounds are shown below:

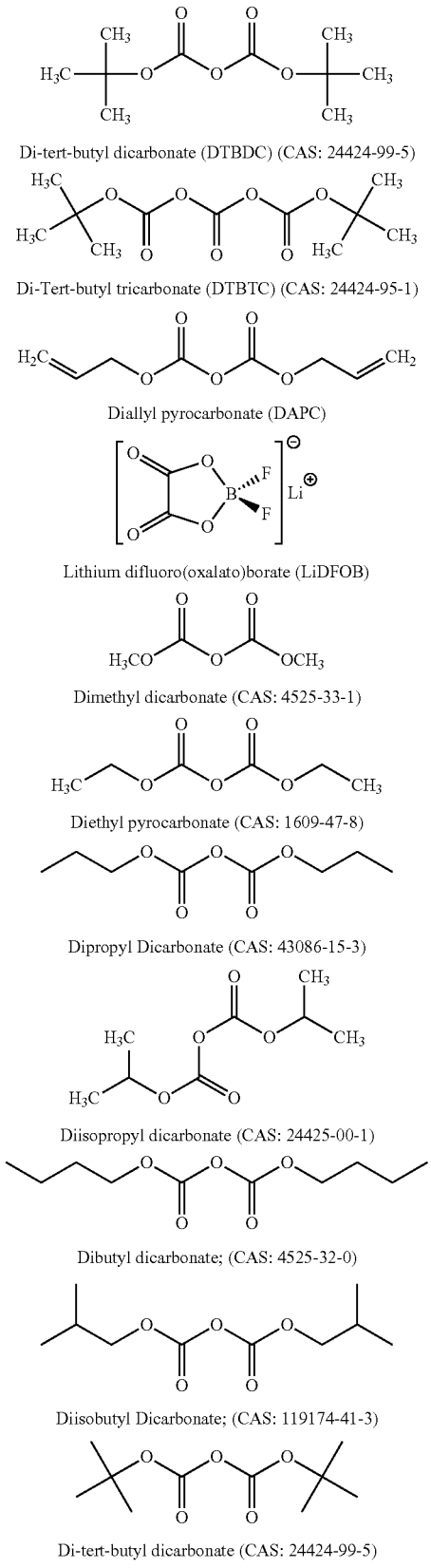

Di-tert-butyl dicarbonate (DTBDC) (CAS: 24424-99-5)

Di-Tert-butyl tricarbonate (DTBTC) (CAS: 24424-95-1)

Diallyl pyrocarbonate (DAPC)

Lithium difluoro(oxalato)borate (LiDFOB)

Dimethyl dicarbonate (CAS: 4525-33-1)

Diethyl pyrocarbonate (CAS: 1609-47-8)

Dipropyl Dicarbonate (CAS: 43086-15-3)

Diisopropyl dicarbonate (CAS: 24425-00-1)

Dibutyl dicarbonate; (CAS: 4525-32-0)

Diisobutyl Dicarbonate; (CAS: 119174-41-3)

Di-tert-butyl dicarbonate (CAS: 24424-99-5)

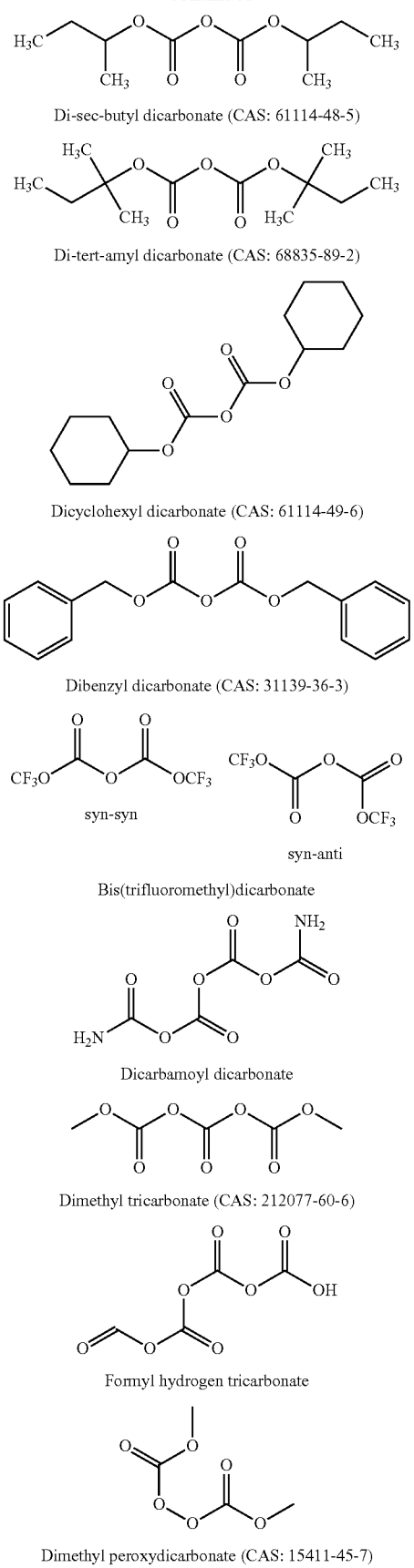

Di-sec-butyl dicarbonate (CAS: 61114-48-5)

Di-tert-amyl dicarbonate (CAS: 68835-89-2)

Dicyclohexyl dicarbonate (CAS: 61114-49-6)

Dibenzyl dicarbonate (CAS: 31139-36-3)

Bis(trifluoromethyl)dicarbonate

Dicarbamoyl dicarbonate

Dimethyl tricarbonate (CAS: 212077-60-6)

Formyl hydrogen tricarbonate

Dimethyl peroxydicarbonate (CAS: 15411-45-7)

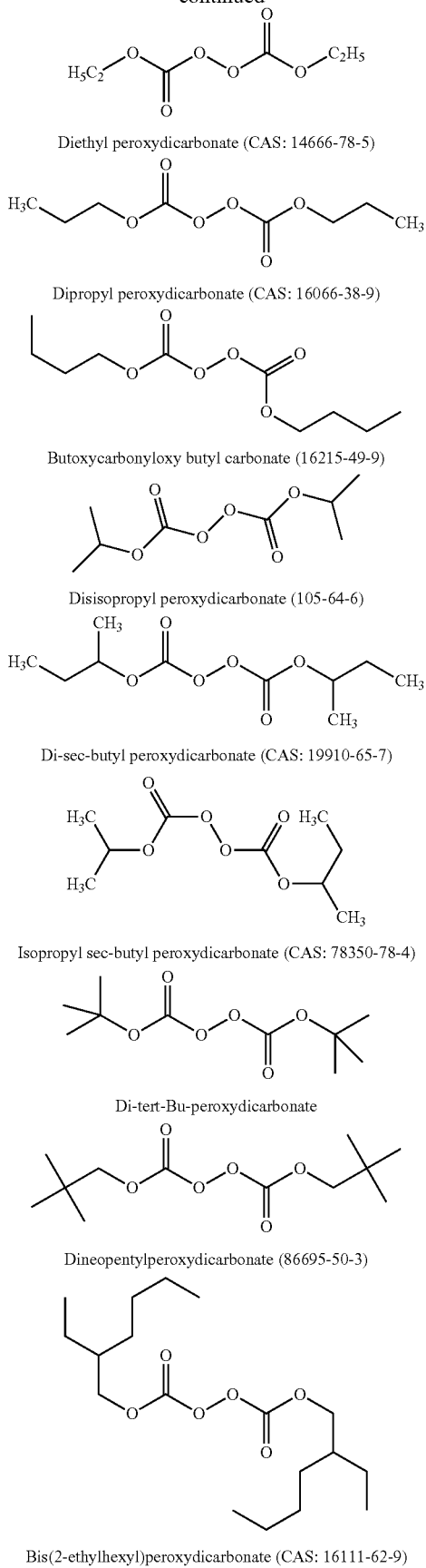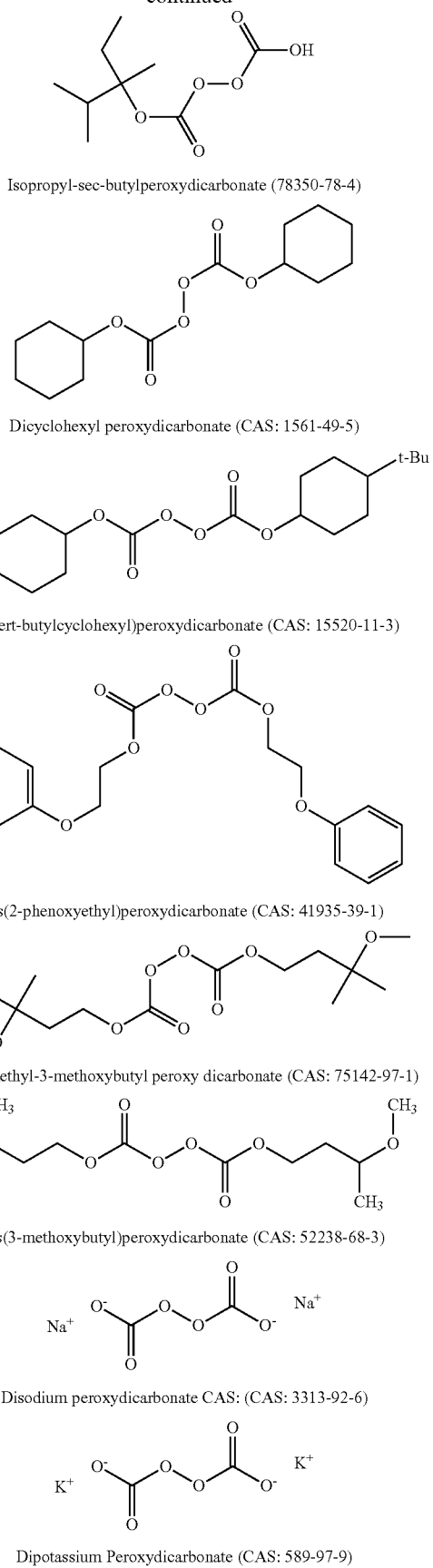

-continued

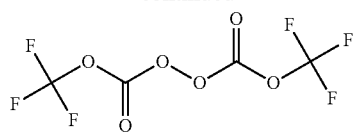

Trifluoromethoxycarbonyloxy trifluoromethyl carbonate

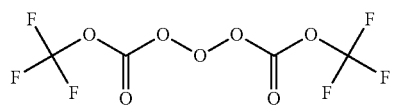

Bis(trifluoromethyl)trioxidicarbonate

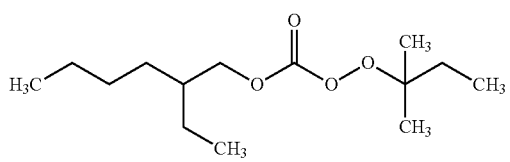

tert-Amylperoxy 2-ethylhexyl carbonate (CAS: 70833-40-8)

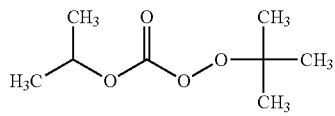

tert-Butylperoxy isopropyl carbonate (CAS: 2372-21-6)

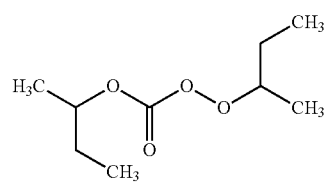

Di-sec-butyl peroxycarbonate (CAS: 71501-14-9)

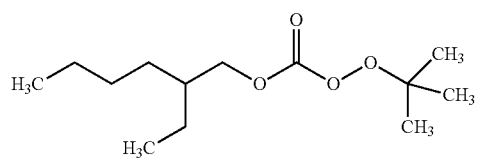

tert-Butylperoxy 2-ethylhexyl carbonate (CAS: 34443-12-4)

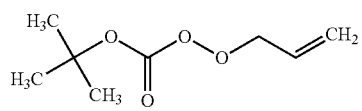

Allyl tert-butyl peroxycarbonate (CAS: 65700-08-5)

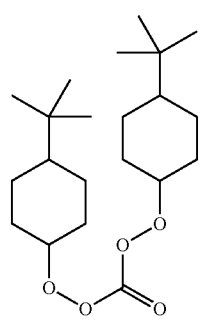

Bis[(4-tert-butylcyclohexyl)oxy]carbonate (CAS: 71331-99-2)

-continued

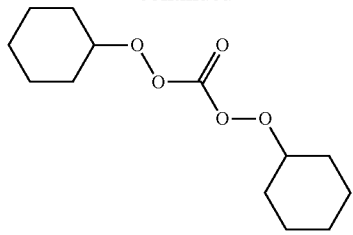

Dicyclohexyl diperoxycarbonate (CAS: 2036-92-2)

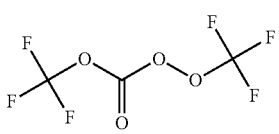

Trifluoro{[(trifluoromethoxy)carbonyl]peroxy}methane

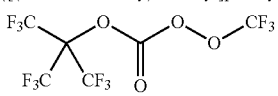

O-[2,2,2-trifluoro-1,1-bis(trifluoro-methyl)ethyl]-
O,O-(trifluoromethyl)peroxycarbonate
(CAS: 55100-93-1)

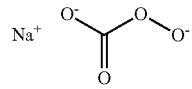

Sodium peroxocarbonate (CAS: 14455-47-1)

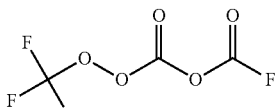

Carbonofluoridoyl Trifluoromethoxy Carbonate

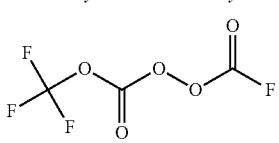

Carbonofluoridoyloxy trifluoromethyl carbonate

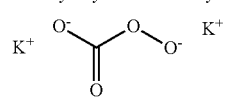

Potassium peroxocarbonate

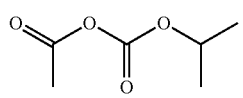

Acetyl isopropyl carbonate (CAS: 60059-18-9)

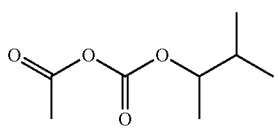

Acetyl 1,2-dimethylpropyl carbonate (CAS: 76085-66-0)

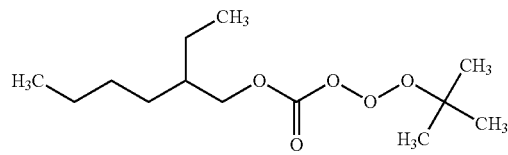

2-Ethylhexyl 3-tert-butyltrioxidane-1-carboxylate

-continued

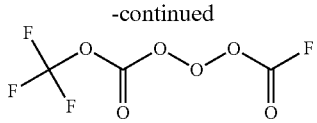

Carbonofluoridoylperoxy Trifluoromethyl Carbonate

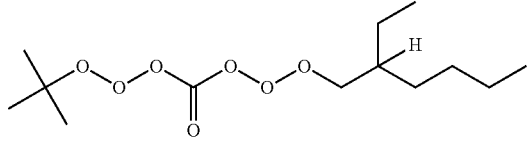

Tert-butylperoxy 2-ethylhexylperoxy carbonate

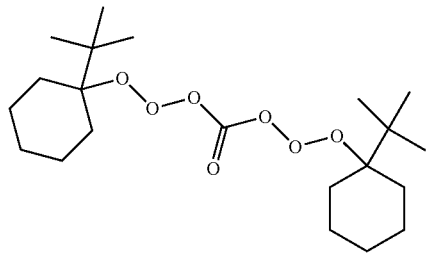

Bis[(1-tert-butylcyclohexyl)peroxy]carbonate

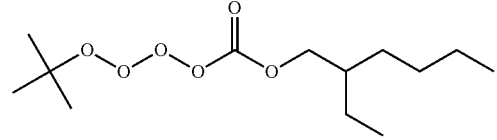

2-Ethylhexyl (2-methylpropan-2-yl)oxyperoxy carbonate

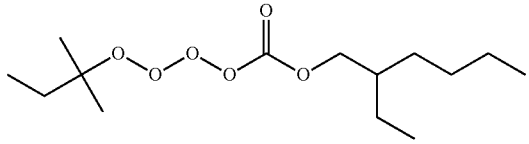

2-Ethylhexyl 2-methylbutan-2-yloxyperoxy carbonate

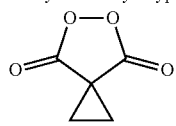

Cyclopropane malonyl peroxide

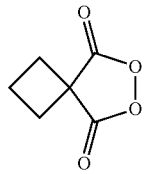

Cyclobutane malonyl peroxide (CAS: 34867-87-3)

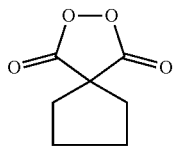

Cyclopentane malonoyl peroxide

Malonoyl peroxide

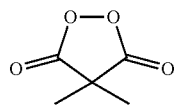

Dimethylmalonyl peroxide

Diethylmalonyl peroxide

-continued

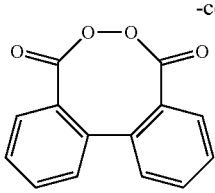

Diphenoyl peroxide

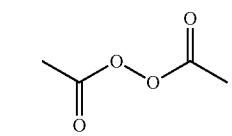

Acetyl peroxide (CAS: 110-22-5)

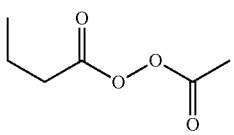

Acetyl butaneperoxoate (CAS: 13043-83-9)

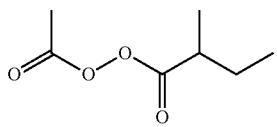

Acetyl 2-methylbutyryl peroxide (CAS: 76085-60-4)

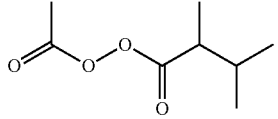

Acetyl 2,3-dimethylbutyryl peroxide (CAS: 76085-62-6)

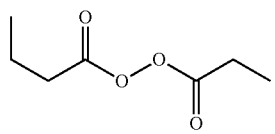

Propanoyl butaneperoxoate (CAS: 13043-86-2)

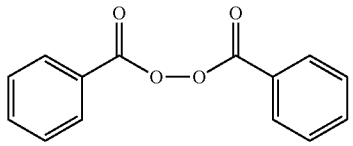

Benzoyl peroxide (BPO) (CAS: 94-36-0)

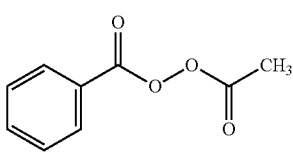

Acetyl benzoyl peroxide (CAS: 644-31-5)

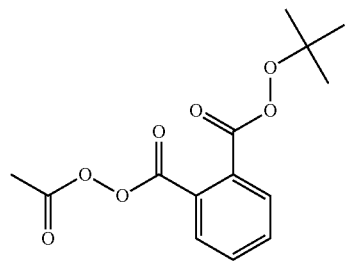

1-O-acetyl 2-O-tert-butyl benzene-1,2-dicarboperoxoate

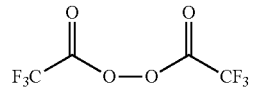

Bis(trifluoroacetyl)peroxide (CAS: 383-73-3)

-continued

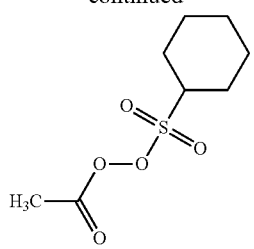

Acetyl cyclohexanesulfonyl peroxide (CAS: 3179-56-4)

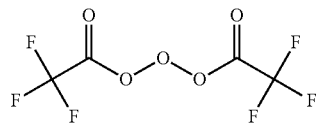

(2,2,2-Trifluoroacetyl)oxy 2,2,2-trifluoroethaneperoxoate

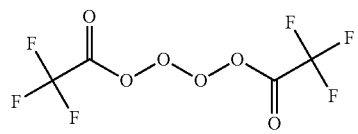

(2,2,2-Trifluoroacetyl)peroxy 2,2,2-trifluoroethaneperoxoate
(CAS: 684-80-0)

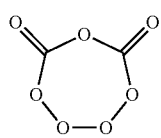

1,2,3,4,6-Pentaoxepane-5,7-dione

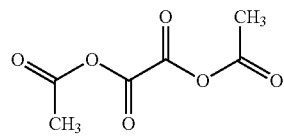

Acetic oxalic anhydride (CAS: 19037-85-5)

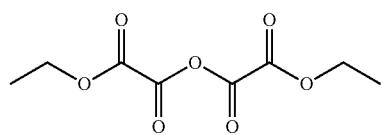

2-Ethoxy-2-oxoacetic anhydride (CAS: 119174-42-4)

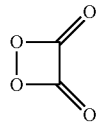

1,2-Dioxetane-3,4-dione (CAS: 26974-08-3)

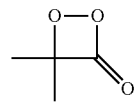

3,3-Dimethyl-1,2-dioxetanone

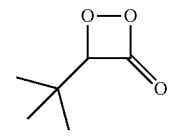

3-Tert-butyl-1,2-dioxetanone

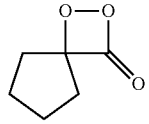

spiro-Cyclopentyl-1,2-dioxetanone

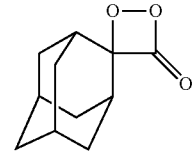

spiro-Adamantyl-1,2-dioxetanone

-continued

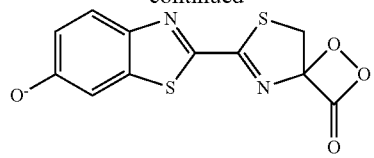

Firefly dioxetanone

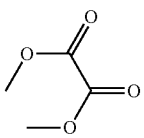 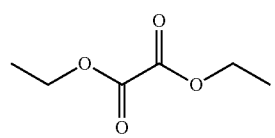

Dimethyl oxalate (CAS: 553-90-2)    Diethyl oxalate (CAS: 95-92-1)

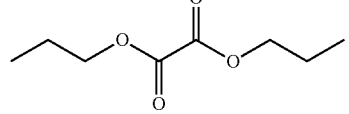

Dipropyl oxalate (CAS: 615-98-5)

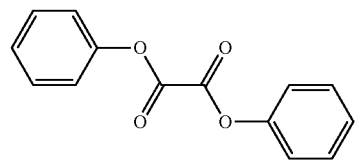

Diphenyl Oxalate (CAS: 3155-16-6)

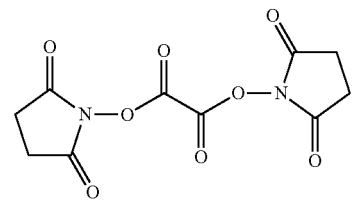

N,N'-Disuccinimidyl oxalate (CAS: 57296-03-4)

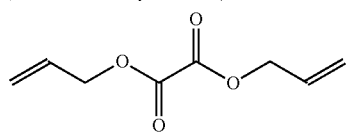

Diallyl oxalate (CAS: 615-99-6)

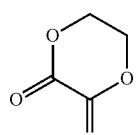 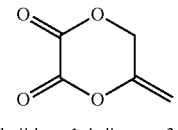

1,4-Dioxane-2,3-dione    5-Methylidene-1,4-dioxane-2,3-dione

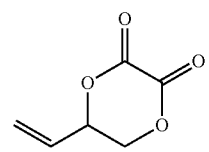

5-Ethenyl-1,4-dioxane-2,3-dione (CAS: 89543-86-2)

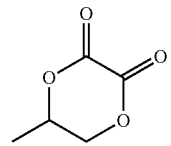

5-Methyl-1,4-dioxane-2,3-dione (CAS: 89093-66-3)

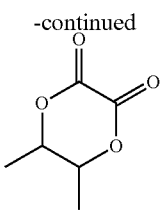

5,6-Dimethyl-1,4-dioxane-2,3-dione (CAS: 89093-67-4)

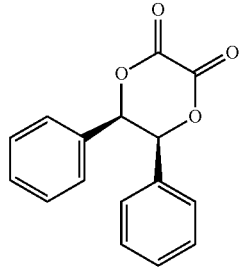

cis-5,6-Diphenyl-1,4-dioxane-2,3-dione (CAS: 74888-53-2)

In some embodiments, a lithium-containing salt for a lithium ion battery may comprise lithium hexafluorophosphate ($LiPF_6$). In some embodiments, a lithium-containing salt for a lithium ion battery may comprise one or more of lithium tetrafluoroborate ($LiBF_4$), lithium hexafluoroarsenate monohydrate ($LiAsF_6$), lithium perchlorate ($LiClO_4$), lithium bis(trifluoromethanesulfonyl)imide (LiTFSI), lithium bis(fluorosulfonyl)imide (LiFSI), lithium bis(oxalato)borate (LiBOB), lithium difluoro(oxalate)borate (LiDFOB), lithium triflate ($LiCF_3SO_3$), lithium tetrafluorooxalato phosphate (LTFOP), lithium difluorophosphate ($LiPO_2F_2$), lithium pentafluoroethyltrifluoroborate (LiFAB), and lithium 2-trifluoromethyl-4,5-dicyanoimidazole (LiTDI), etc. In some embodiments, the electrolyte can have a salt concentration of about 1 moles/L (M).

These electrolyte additives, along with the electrolytes, can be reduced or self-polymerize on the surface of Si anode to form a SEI layer that can reduce or prevent the crack and/or the continuous reduction of electrolyte solutions as the silicon containing anode expands and contracts during cycling. Furthermore, these electrolyte additives, along with the electrolyte solvents, may be oxidized on a cathode surface to form a CEI layer that can suppress or minimize further decomposition of the electrolyte on the surface of the cathode. Without being bound to the theory or mode of operation, it is believed that the presence of functional compounds in the electrolyte such as a carbonate, oxalate, trioxidane, peroxide, peroxoate, dioxetanone, oxepane dione, oxetane dione, anhydride, oxalate or 1,4-dioxane-2,3-dione, which may be optionally substituted, can result in a SEI and/or CEI layer on the surface of electrodes with improved performance. An SEI layer comprising a carbonate, oxalate, trioxidane, peroxide, peroxoate, dioxetanone, oxepane dione, oxetane dione, anhydride, oxalate or 1,4-dioxane-2,3-dione, which may be optionally substituted, may demonstrate improved chemical stability and increased density, for example, compared to SEI layers formed by electrolytes without additives or with traditional additives. As such, the change in thickness and surface reactivity of the interface layer are limited, which may in turn facilitate reduction in capacity fade and/or generation of excessive gaseous byproducts during operation of the lithium ion battery. A CEI layer comprising a carbonate, oxalate, trioxidane, peroxide, peroxoate, dioxetanone, oxepane dione, oxetane dione, anhydride, oxalate or 1,4-dioxane-2,3-dione, which may be optionally substituted, may demonstrate may help minimize the transition metal ion dissolutions and structure changes on cathode side and may provide favorable kinetics resulting in improved cycling stability and rate capability. In some embodiments, electrolyte solvents comprising a carbonate, oxalate, trioxidane, peroxide, peroxoate, dioxetanone, oxepane dione, oxetane dione, anhydride, oxalate or 1,4-dioxane-2,3-dione, which may be optionally substituted, may be less flammable and more flame retardant.

In some embodiments, a lithium ion battery comprising an electrolyte composition according to one or more embodiments described herein, and an anode having a composite electrode film according to one or more embodiments described herein, may demonstrate reduced gassing and/or swelling at about room temperature (e.g., about 20° C. to about 25° C.) or elevated temperatures (e.g., up to temperatures of about 85° C.), increased cycle life at about room temperature or elevated temperatures, and/or reduced cell growth/electrolyte consumption per cycle, for example compared to lithium ion batteries comprising conventionally available electrolyte compositions in combination with an anode having a composite electrode film according to one or more embodiments described herein. In some embodiments, a lithium ion battery comprising an electrolyte composition according to one or more embodiments described herein and an anode having a composite electrode film according to one or more embodiments described herein may demonstrate reduced gassing and/or swelling across various temperatures at which the battery may be subject to testing, such as temperatures between about −20° C. and about 130° C. (e.g., compared to lithium ion batteries comprising conventionally available electrolyte compositions in combination with an anode having a composite electrode film according to one or more embodiments described herein).

Gaseous byproducts may be undesirably generated during battery operation, for example, due to chemical reactions between the electrolyte and one or more other components of the lithium ion battery, such as one or more components of a battery electrode. Excessive gas generation during operation of the lithium ion battery may adversely affect battery performance and/or result in mechanical and/or electrical failure of the battery. For example, undesired chemical reactions between an electrolyte and one or more components of an anode may result in gas generation at levels which can mechanically (e.g., structural deformation) and/or electrochemically degrade the battery. In some embodiments, the composition of the anode and the composition of the electrolyte can be selected to facilitate desired gas generation.

The electrolytes and electrolyte additives described herein may be advantageously utilized within an energy storage device. In some embodiments, energy storage devices may include batteries, capacitors, and battery-capacitor hybrids. In some embodiments, the energy storage device comprise lithium. In some embodiments, the energy storage device may comprise at least one electrode, such as an anode and/or cathode. In some embodiments, at least one electrode may be a Si-based electrode. In some embodiments, the Si-based electrode is a Si-dominant electrode, where silicon is the majority of the active material used in the electrode (e.g., greater than 50% silicon). In some embodiments, the energy storage device comprises a separator. In some embodiments, the separator is between a first electrode and a second electrode.

In some embodiments, the energy storage device comprises an electrolyte. In some embodiments, the electrolyte comprises a solvent, solvent additive and/or compound as described previously herein. For example, in some embodiments, the electrolyte comprises a cyclic organosilicon compound as described previously herein.

As described herein, a battery can be implemented as a pouch cell. FIG. 1 shows a cross-sectional schematic diagram of an example of a lithium ion battery 300 implemented as a pouch cell, according to some embodiments. The battery 300 comprises an anode 316 in contact with a negative current collector 308, a cathode 304 in contact with a positive current collector 310, a separator 306 disposed between the anode 316 and the cathode 304. In some embodiments, a plurality of anodes 316 and cathode 304 may be arranged into a stacked configuration with a separator 306 separating each anode 316 and cathode 304. Each negative current collector 308 may have one anode 316 attached to each side; each positive current collector 310 may have one cathode 304 attached to each side. The stacks are immersed in an electrolyte 314 and enclosed in a pouch 312. The anode 302 and the cathode 304 may comprise one or more respective electrode films formed thereon. The number of electrodes of the battery 300 may be selected to provide desired device performance.

With further reference to FIG. 1, the separator 306 may comprise a single continuous or substantially continuous sheet, which can be interleaved between adjacent electrodes of the electrode stack. For example, the separator 306 may be shaped and/or dimensioned such that it can be positioned between adjacent electrodes in the electrode stack to provide desired separation between the adjacent electrodes of the battery 300. The separator 306 may be configured to facilitate electrical insulation between the anode 302 and the cathode 304, while permitting ionic transport between the anode 302 and the cathode 304. In some embodiments, the separator 306 may comprise a porous material, including a porous polyolefin material.

The lithium ion battery 300 may include an electrolyte 314, for example an electrolyte having a composition as described herein. The electrolyte 314 is in contact with the anode 302, the cathode 304, and the separator 306.

With continued reference to FIG. 1, the anode 302, cathode 304 and separator 306 of the lithium ion battery 300 may be enclosed in a housing comprising a pouch 312. In some embodiments, the pouch 312 may comprise a flexible material. For example, the pouch 312 may readily deform upon application of pressure on the pouch 312, including pressure exerted upon the pouch 312 from within the housing. In some embodiments, the pouch 312 may comprise aluminum. For example, the pouch 312 may comprise a laminated aluminum pouch.

In some embodiments, the lithium ion battery 300 may comprise an anode connector (not shown) and a cathode connector (not shown) configured to electrically couple the anodes and the cathodes of the electrode stack to an external circuit, respectively. The anode connector and a cathode connector may be affixed to the pouch 312 to facilitate electrical coupling of the battery 300 to an external circuit. The anode connector and the cathode connector may be affixed to the pouch 312 along one edge of the pouch 312. The anode connector and the cathode connector can be electrically insulated from one another, and from the pouch 312. For example, at least a portion of each of the anode connector and the cathode connector can be within an electrically insulating sleeve such that the connectors can be electrically insulated from one another and from the pouch 312.

The below example devices and processes for device fabrication generally described below, and the performances of lithium ion batteries with different electrolytes and electrolyte additives are evaluated.

Example 1

2 wt % Di-tert-butyl dicarbonate (DTBDC), Di-Tert-butyl tricarbonate (DTBTC) or 2 wt % DTBDC/1wt % Lithium difluoro(oxalato)borate (LiDFOB), 2 wt % DTBTC/1 wt % LiDFOB may be added as electrolyte additives to 1.2M LiPF6 in FEC/EMC (3/7 wt %)-based electrolyte for Si-dominant anode//NCA cathode full cells to investigate their electrochemical performance at different temperature ranges. The corresponding 5 layer pouch cells may be created with Si-dominant anodes and NCA cathodes and may be tested using a 0.33 C/0.33 C charge/discharge cycle regime with the working voltage window of 4.2V to 3.3V at −20° C.

Figure 2A:
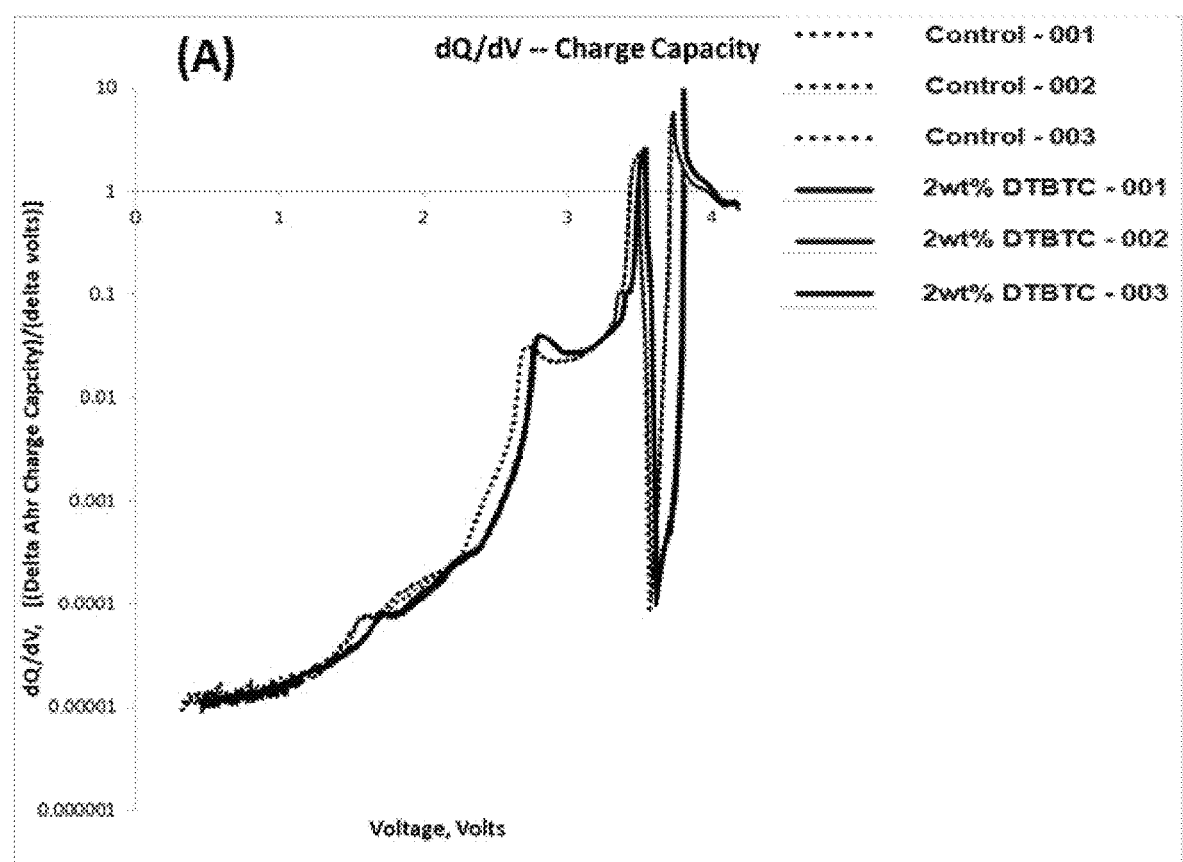
FIGS. 2A and 2B show dQ/dV curve—During Charge (FIG. 2A) and dQ/dV curve—During Discharge (FIG. 2B) of Si-dominant anode//NCA cathode full cells tested at room temperature. The electrolytes used may be: (dotted line) 1.2 M LiPF6 in FEC/EMC (3/7 wt %)—Control, (solid line) 1.2M LiPF$_6$ in FEC/EMC (3/7 wt %)+2 wt % DTBTC, in accordance with an example embodiment of the disclosure.
Figure 2B:
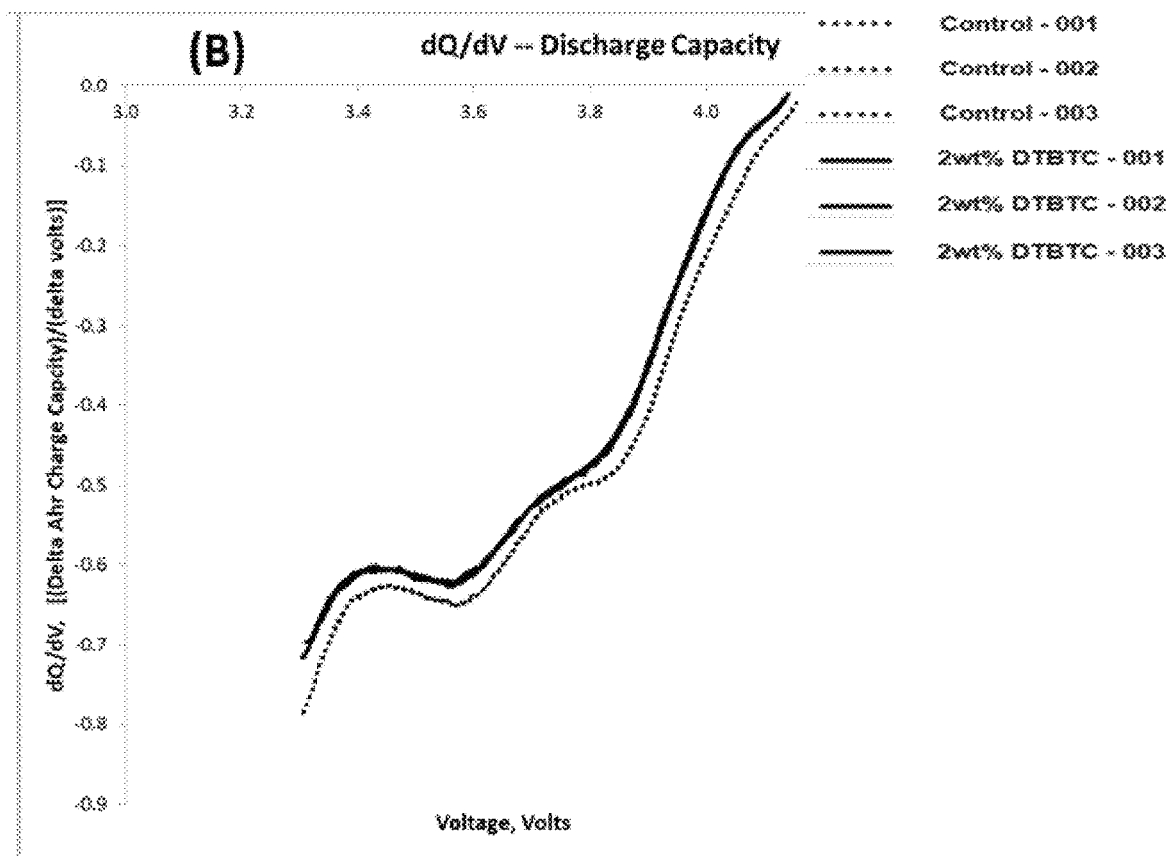

FIG. 2. dQ/dV—During Charge (FIG. 2A) and dQ/dV—During Discharge (FIG. 2B) curves of Si-dominant anode//NCA cathode full cells tested at room temperature. The electrolytes used may be: (dotted line) 1.2 M $LiPF_6$ in FEC/EMC (3/7 wt %)—Control, (solid line) 1.2M $LiPF_6$ in FEC/EMC (3/7 wt %)+2 wt % DTBTC. The Si-dominant anodes contain about 80 wt % Si, 5 wt % graphite and 15 wt % glassy carbon (from resin), and may be laminated on 15 μm Cu foil. The average loading is about 2-5 mg/cm$^2$. The cathodes contain about 92 wt % NCA, 4 wt % Super P and 4 wt % PVDF5130, and may be coated on 15 μm Al foil. The average loading is about 20-30 mg/cm$^2$.

The dQ/dV data for both control and 2 wt % DTBTC-containing cells may be obtained through the following testing protocol: Charge at 0.025 C to 25% nominal capacity, charge at 1 C to 4.2 V until 0.05 C, discharge at 1 C to 3.3 V.

The 1$^{st}$ formation cycle dQ/dV curves in FIG. 2 show that 2 wt % DTBTC-containing cells have different reaction peaks indicating differences in electrode electrolyte interface formation.

Figure 3A:
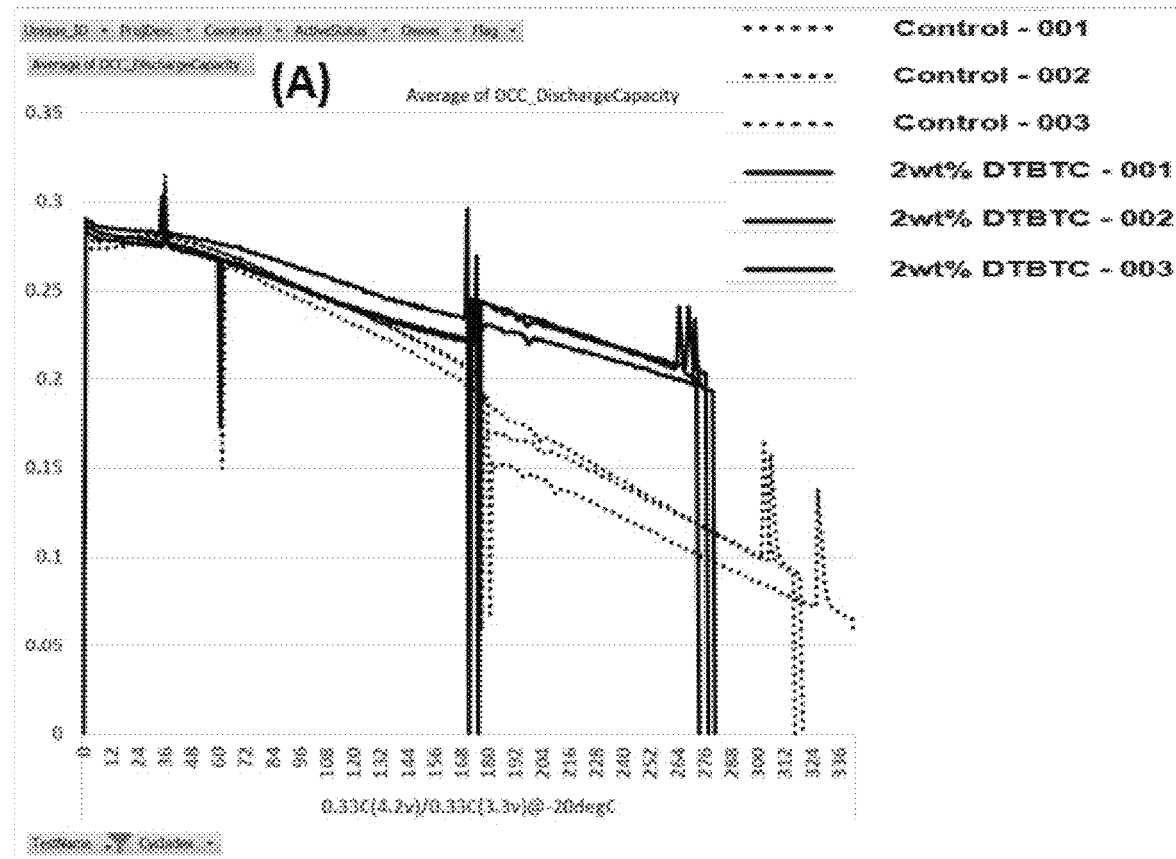
FIGS. 3A and 3B show the capacity retention (FIG. 3A) and normalized capacity retention (FIG. 3B) of Si-dominant anode//NCA cathode full cells tested at −20° C. using 2 wt % DTBTC, in accordance with an example embodiment of the disclosure.
Figure 3B:
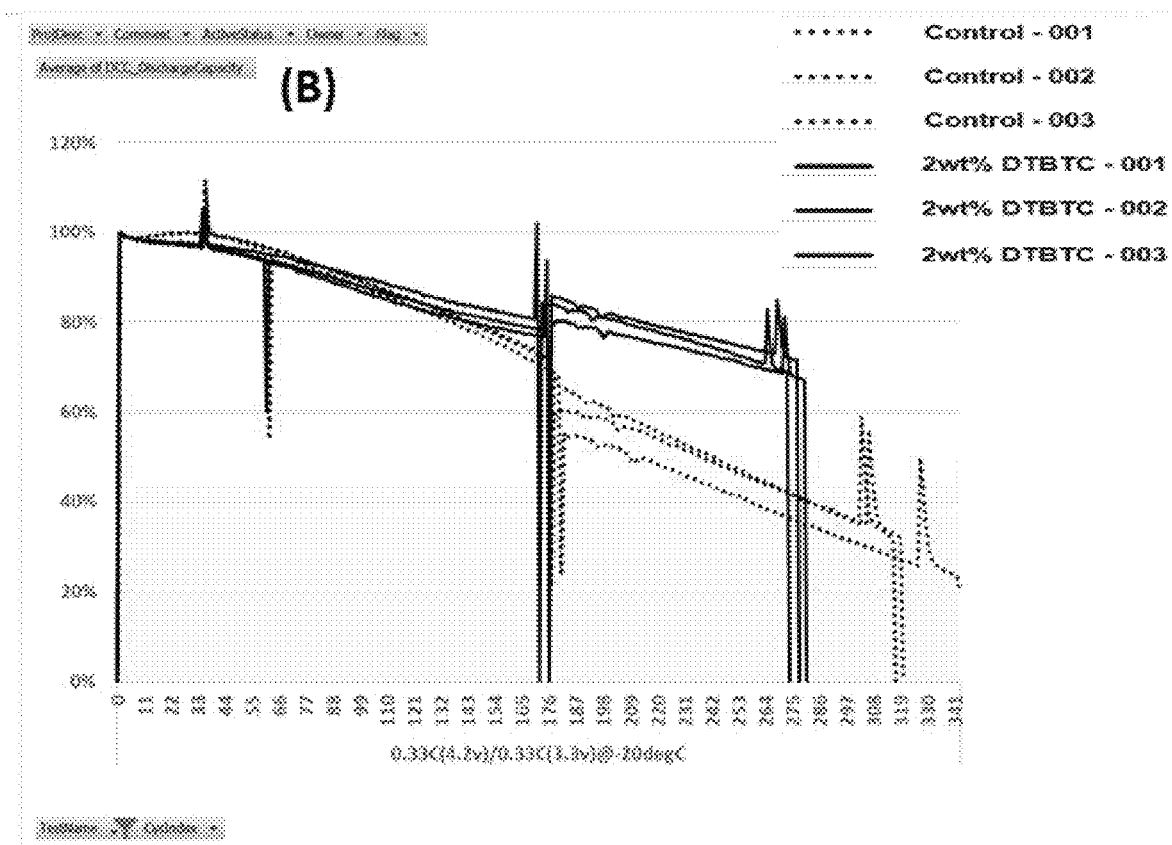

FIG. 3. Capacity retention (FIG. 3A) and Normalized capacity retention (FIG. 3B) of Si-dominant anode//NCA cathode full cells tested at −20° C. The Si-dominant anodes contain about 80 wt % Si, 5 wt % graphite and 15 wt % glassy carbon (from resin), and may be laminated on 15 μm Cu foil. The average loading is about 2-5 mg/cm$^2$. The testing temperature may be −20° C.

The long-term cycling program for both control and 2 wt % DTBTC-containing cells include: Charge at 0.33 C to 4.2 V until 0.05 C, rest 10 minutes, discharge at 0.33 C to 3.3 V, rest 10 minutes.

FIG. 3 indicates that when adding 2 wt % DTBTC into 1.2 M $LiPF_6$ in FEC/EMC (3/7 wt %)-based electrolytes, the corresponding cell capacity retention is improved compared with reference electrolyte-based control cells.

Figure 4A:
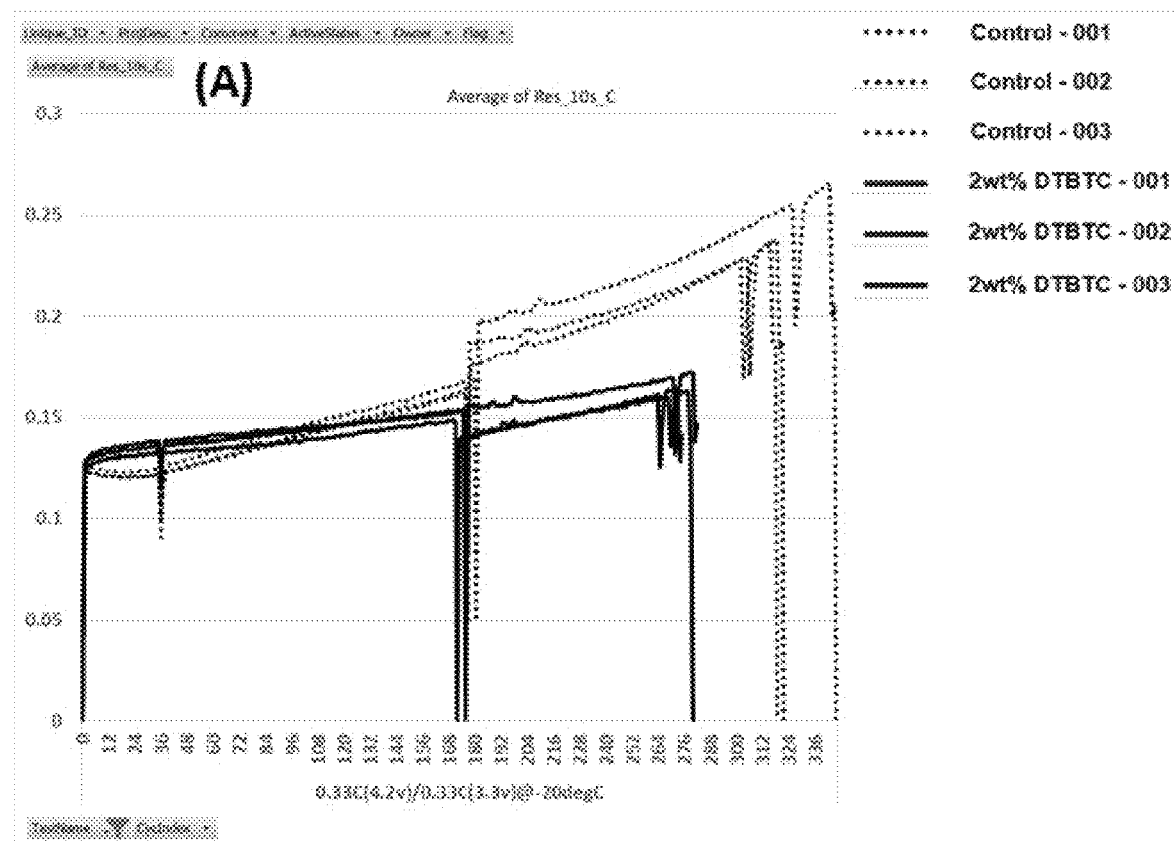
FIGS. 4A and 4B show average 10 second internal resistance for 10 s pulses during charge (FIG. 4A) and discharge (FIG. 4B) processes of Si-dominant anode//NCA cathode full cells tested at −20° C. The electrolytes used may be: (dotted line) 1.2 M LiPF6 in FEC/EMC (3/7 wt %)—Control, (thick solid line) 1.2M LiPF6 in FEC/EMC (3/7 wt %)+2 wt % DTBTC, in accordance with an example embodiment of the disclosure.
Figure 4B:
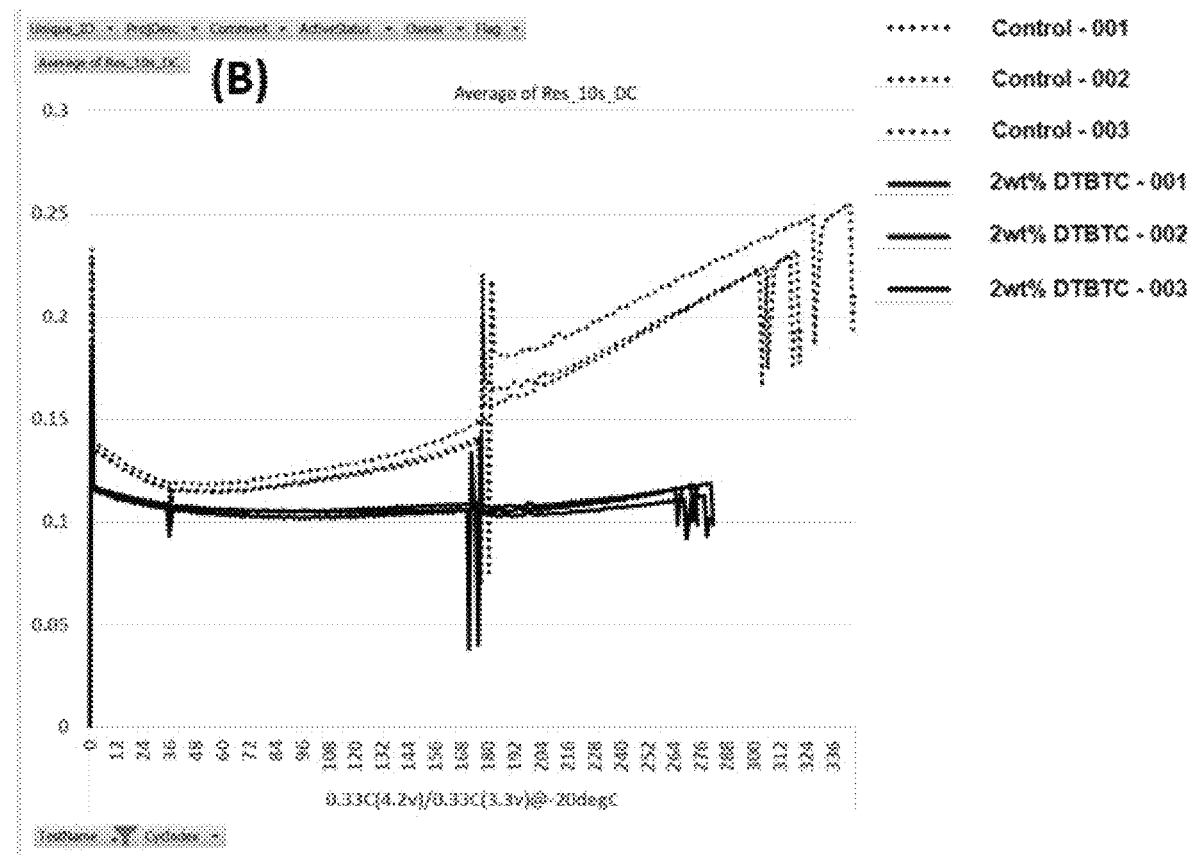

FIG. 4. Average 10 second internal resistance for 10 s pulses during charge (FIG. 4A) and discharge (FIG. 4B) processes of Si-dominant anode//NCA cathode full cells tested at −20° C. The electrolytes used may be: (dotted line) 1.2 M $LiPF_6$ in FEC/EMC (3/7 wt %)—Control, (thick solid line) 1.2M $LiPF_6$ in FEC/EMC (3/7 wt %)+2 wt % DTBTC. The testing temperature is −20° C. The Res fields are values calculated by using data points of voltage and current. It linearly interpolates for a voltage at the 10 s in the charge/ discharge step between the two data points before and after that time. Then it takes the difference between that voltage and the last voltage during rest when current is 0 and divides it by the charge or discharge current.

Res_10s_C is calculated using discharge data (for the charged state).

Res_10s_DC is calculated using charge data (for the cell state at the beginning of the cycle).

The results in FIG. 4 show that 2 wt % DTBTC-containing cells have lower resistance increase than reference electrolyte-based control cells with the increase of cycling.

Figure 5A:
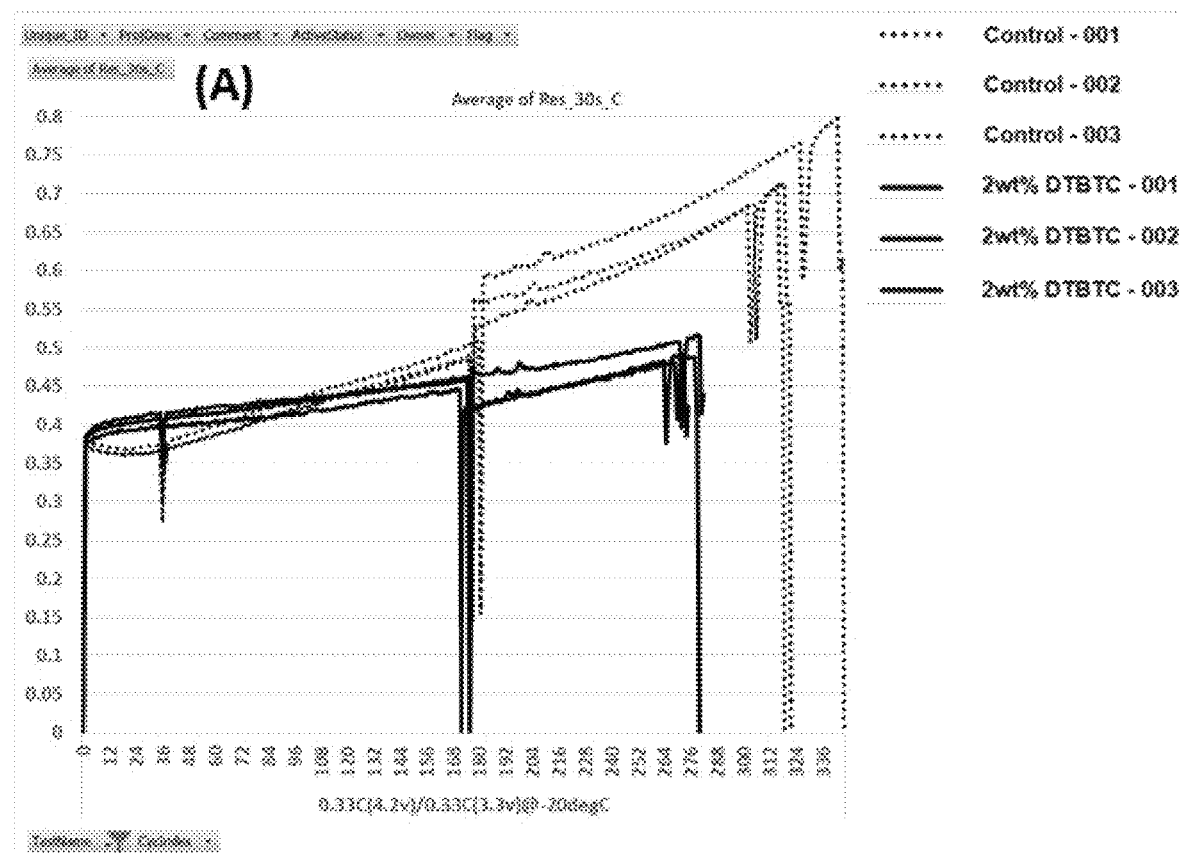
FIGS. 5A and 5B show average resistance during 30 s pulses for the charge (FIG. 5A) and discharge (FIG. 5B) processes of Si-dominant anode//NCA cathode full cells tested at −20° C. The electrolytes used may be: (dotted line) 1.2 M LiPF6 in FEC/EMC (3/7 wt %)—Control, (thick solid line) 1.2M LiPF$_6$ in FEC/EMC (3/7 wt %)+2 wt % DTBTC, in accordance with an example embodiment of the disclosure.
Figure 5B:
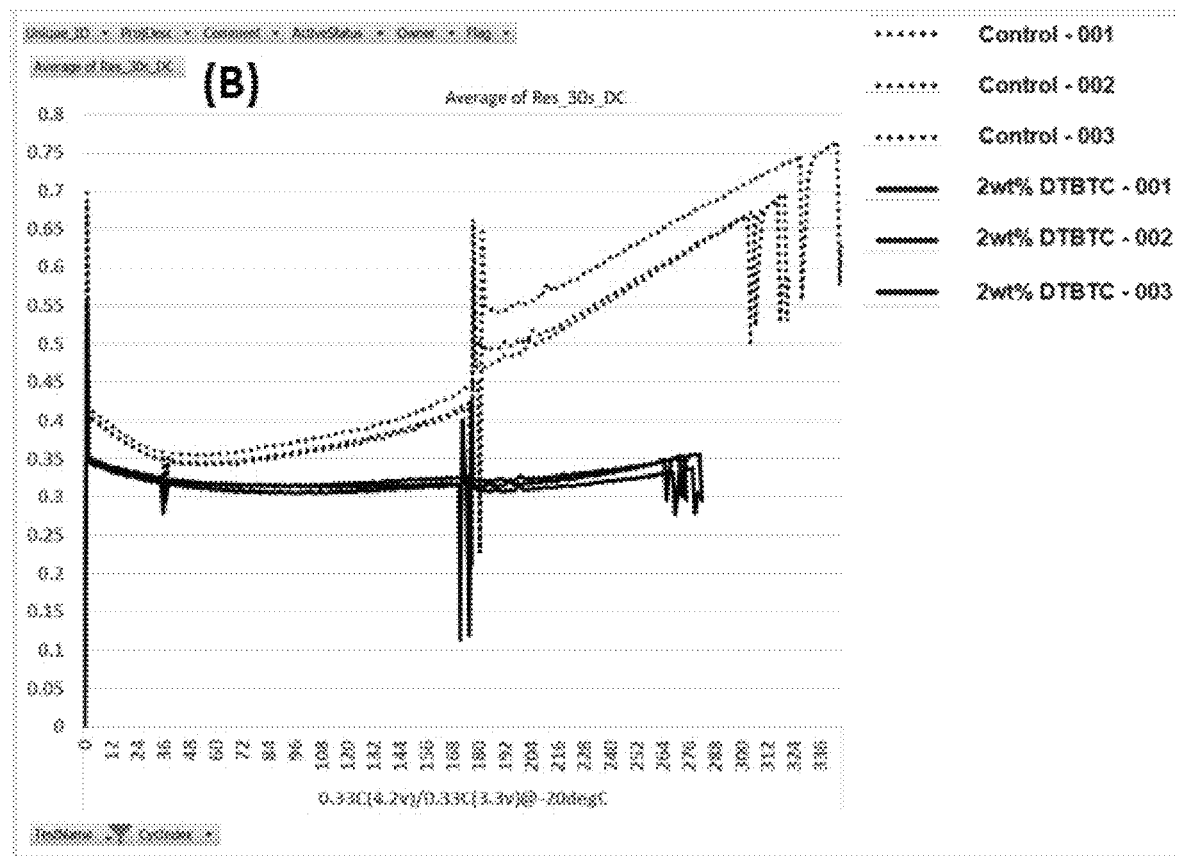

FIG. 5. Average resistance during 30s pulses for the charge (FIG. 5A) and discharge (FIG. 5B) processes of Si-dominant anode//NCA cathode full cells tested at −20° C. The electrolytes used may be: (dotted line) 1.2 M $LiPF_6$ in FEC/EMC (3/7 wt %)—Control, (thick solid line) 1.2M $LiPF_6$ in FEC/EMC (3/7 wt %)+2 wt % DTBTC. The testing temperature is −20° C.

The Res fields are values calculated by using data points of voltage and current. It linearly interpolates for a voltage at the 30 s in the charge/discharge step between the two data points before and after that time. Then it takes the difference between that voltage and the last voltage during rest when current is 0 and divides it by the charge or discharge current.

Res_30s_C is calculated using discharge data (for the charged state).

Res_30s_DC is calculated using charge data (for the cell state at the beginning of the cycle).

The results in FIG. 5 show that 2 wt % DTBTC-containing cells have lower resistance increase than reference electrolyte-based control cells with the increase of cycling.

Example 2

Figure 6A:
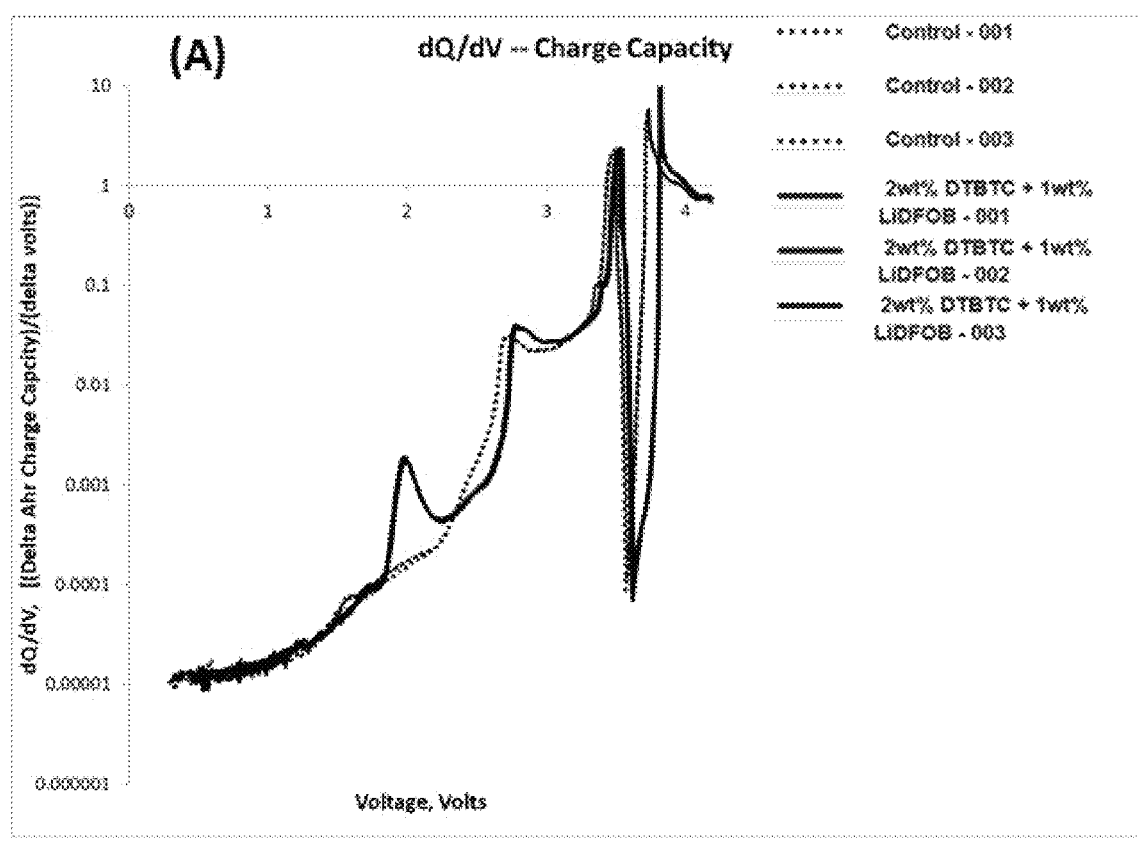
FIGS. 6A and 6B show dQ/dV curve—During Charge (FIG. 6A) and dQ/dV curve—During Discharge (FIG. 6B) of Si-dominant anode//NCA cathode full cells tested at room temperature. The electrolytes used may be: (dotted line) 1.2 M LiPF$_6$ in FEC/EMC (3/7 wt %)—Control, (solid line) 1.2M LiPF$_6$ in FEC/EMC (3/7 wt %)+2 wt % DTBTC+1 wt % LiDFOB, in accordance with an example embodiment of the disclosure.
Figure 6B:
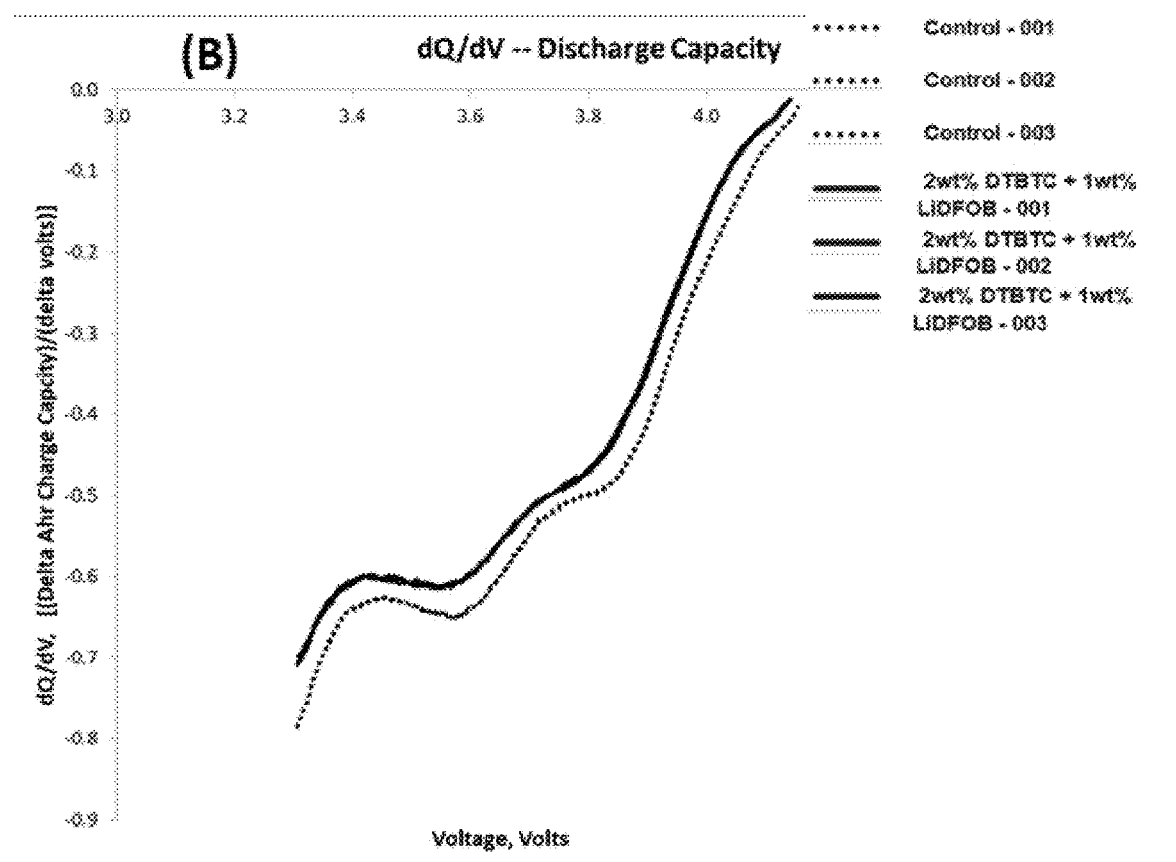

FIG. 6. dQ/dV—During Charge (FIG. 6A) and dQ/dV—During Discharge (FIG. 6B) curves of Si-dominant anode//NCA cathode full cells tested at room temperature. The electrolytes used may be: (dotted line) 1.2 M $LiPF_6$ in FEC/EMC (3/7 wt %)—Control, (solid line) 1.2M $LiPF_6$ in FEC/EMC (3/7 wt %)+2 wt % DTBTC+1 wt % LiDFOB. The Si-dominant anodes contain about 80 wt % Si, 5 wt % graphite and 15 wt % glassy carbon (from resin), and may be laminated on 15 μm Cu foil. The average loading is about 2-5 mg/cm². The cathodes contain about 92 wt % NCA, 4 wt % Super P and 4 wt % PVDF5130, and may be coated on 15 μm Al foil. The average loading is about 20-30 mg/cm².

The dQ/dV data for both control and 2 wt % DTBTC+1 wt % LiDFOB-containing cells may be obtained through the same testing protocol as the above mentioned in FIG. 2.

The 1$^{st}$ formation cycle dQ/dV curves in FIG. 6 show that 2 wt % DTBTC+1 wt % LiDFOB-containing cells have strong peak around 2V which suggests a very different SEI layer is formed, relative to the SEI layer formed in FIG. 2, due to the presence of LiDFOB salt in the electrolyte formulation.

Figure 7A:
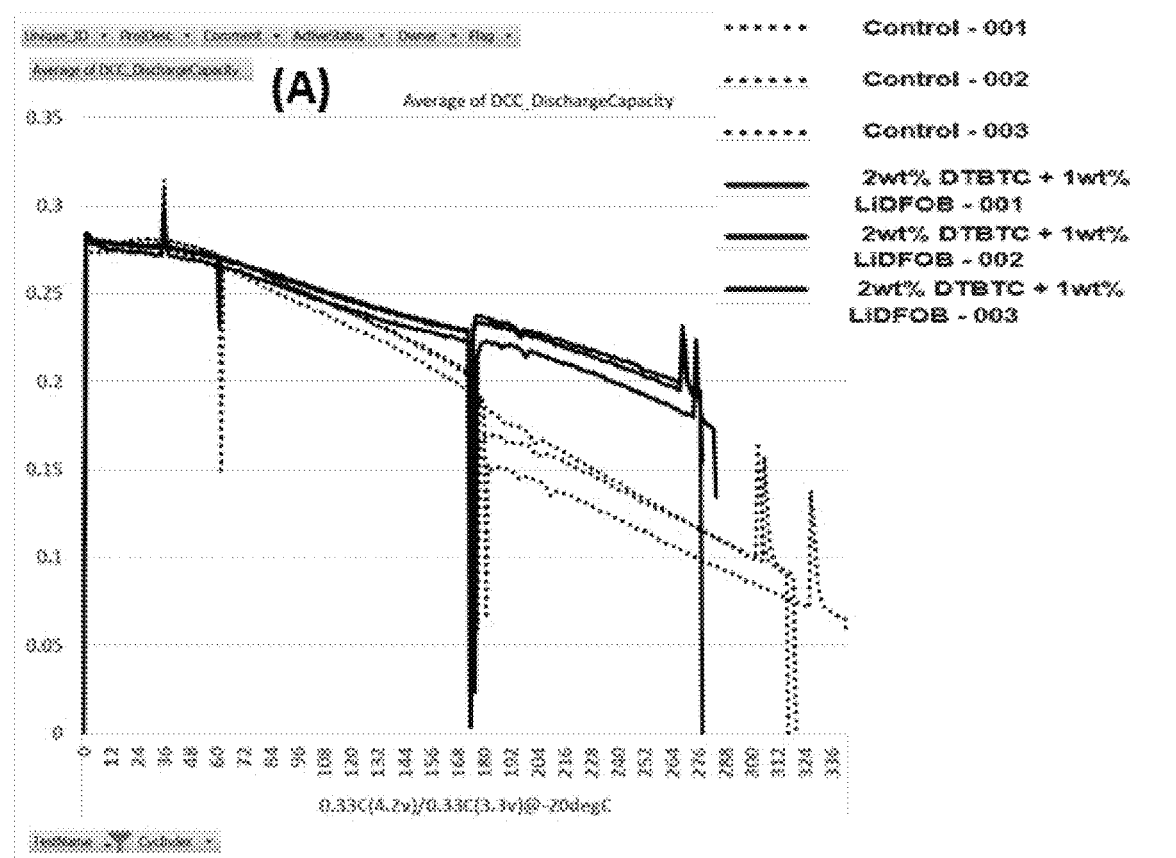
FIGS. 7A and 7B show the capacity retention (FIG. 7A) and normalized capacity retention (FIG. 7B) of Si-dominant anode//NCA cathode full cells tested at −20° C. using 2 wt % DTBTC+1 wt % LiDFOB, in accordance with an example embodiment of the disclosure.
Figure 7B:
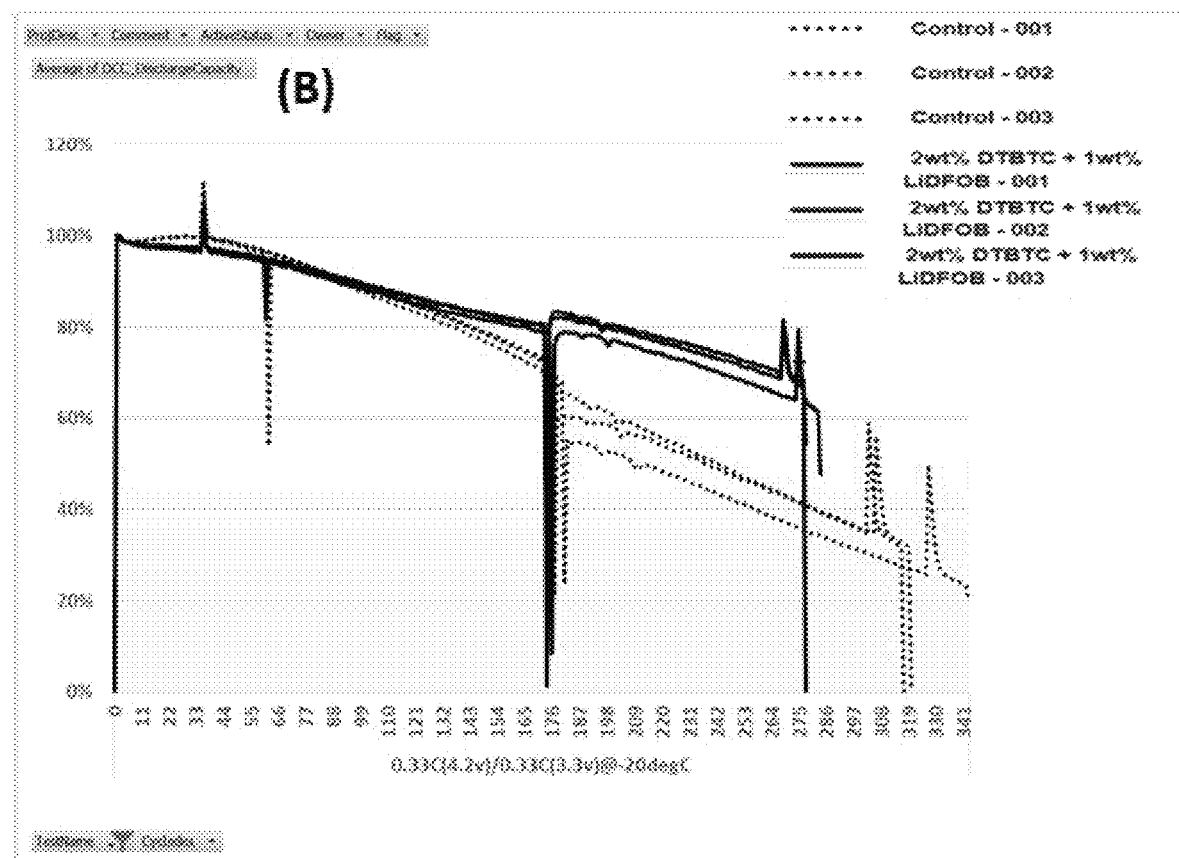

FIG. 7. Capacity retention (FIG. 7A) and Normalized capacity retention (FIG. 7B) of Si-dominant anode//NCA cathode full cells tested at −20° C. The Si-dominant anodes contain about 80 wt % Si, 5 wt % graphite and 15 wt % glassy carbon (from resin), and may be laminated on 15 μm Cu foil. The average loading is about 2-5 mg/cm². The testing temperature may be −20° C.

The long-term cycling program for both control and 2 wt % DTBTC+1 wt % LiDFOB-containing cells are the same as the above mentioned in FIG. 3.

FIG. 7 indicates that when adding 2 wt % DTBTC+1 wt % LiDFOB into 1.2 M $LiPF_6$ in FEC/EMC (3/7 wt %)-based electrolytes, the corresponding cell capacity retention is improved compared with reference electrolyte-based control cells.

Figure 8A:
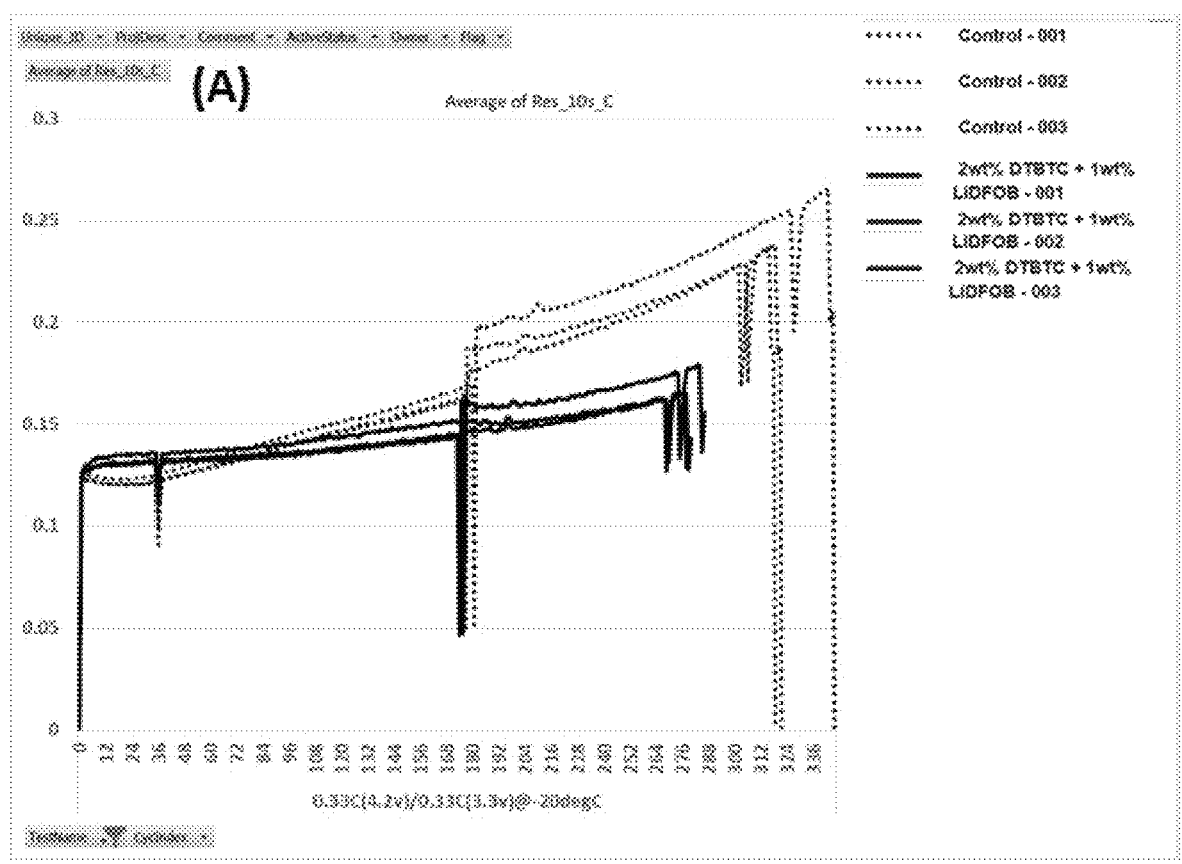
FIGS. 8A and 8B show average 10 second internal resistance for 10 s pulses during charge (FIG. 8A) and discharge (FIG. 8B) processes of Si-dominant anode//NCA cathode full cells tested at −20° C. The electrolytes used may be: (dotted line) 1.2 M LiPF6 in FEC/EMC (3/7 wt %)—Control, (thick solid line) 1.2M LiPF6 in FEC/EMC (3/7 wt %)+2 wt % DTBTC+1 wt % LiDFOB, in accordance with an example embodiment of the disclosure.
Figure 8B:
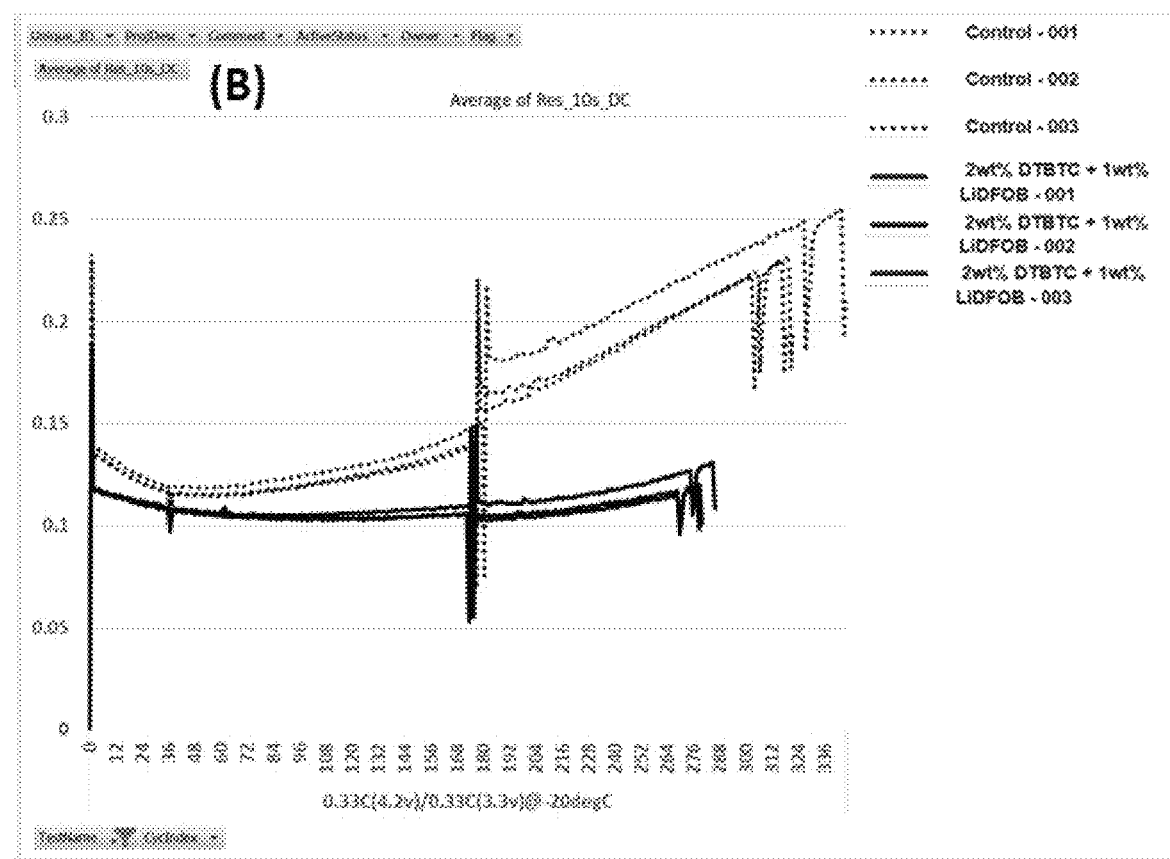

FIG. 8. Average 10 second internal resistance for 10 s pulses during charge (FIG. 8A) and discharge (FIG. 8B) processes of Si-dominant anode//NCA cathode full cells tested at −20° C. The electrolytes used may be: (dotted line) 1.2 M $LiPF_6$ in FEC/EMC (3/7 wt %)—Control, (thick solid line) 1.2M $LiPF_6$ in FEC/EMC (3/7 wt %)+2 wt % DTBTC+1 wt % LiDFOB. The testing temperature may be −20° C.

The results in FIG. 8 show that 2 wt % DTBTC+1 wt % LiDFOB-containing cells have lower resistance increase than reference electrolyte-based control cells with the increase of cycling.

Figure 9A:
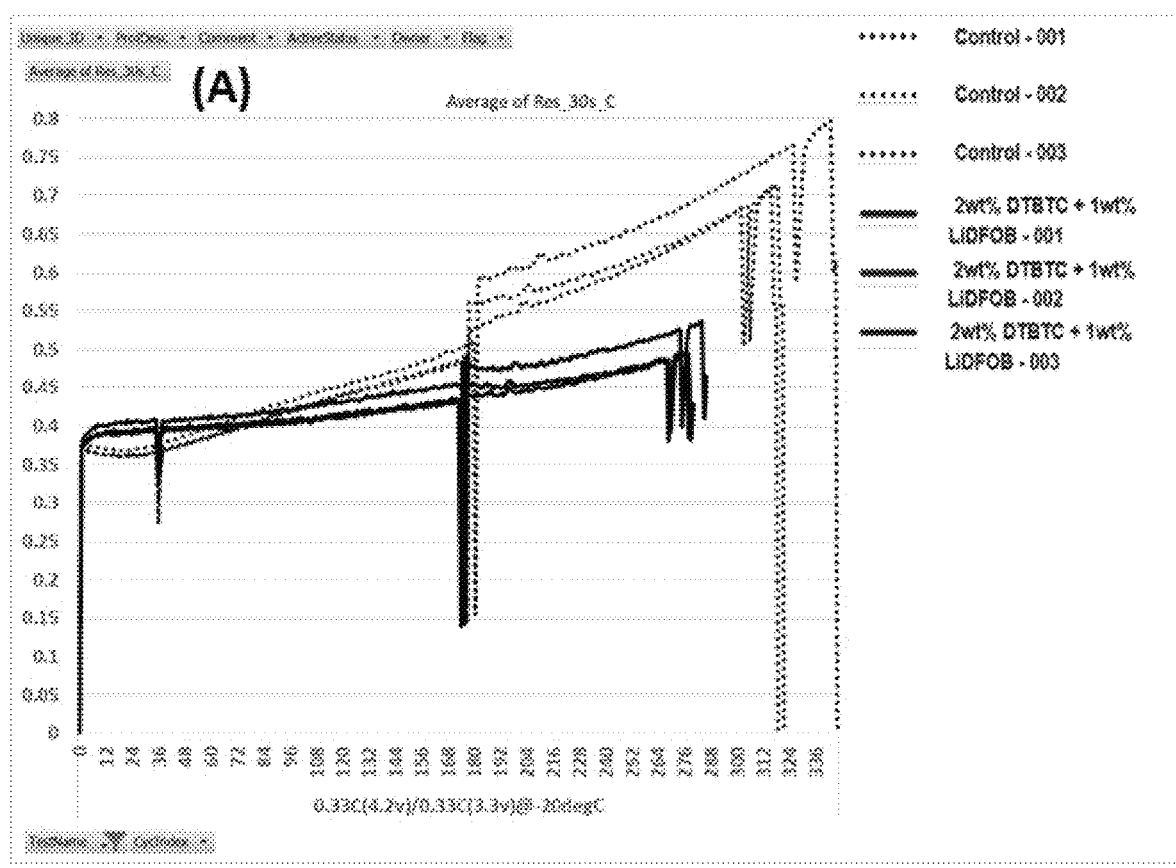
FIGS. 9A and 9B show average resistance during 30 s pulses for the charge (FIG. 9A) and discharge (FIG. 9B) processes of Si-dominant anode//NCA cathode full cells tested at −20° C. The electrolytes used may be: (dotted line) 1.2 M LiPF6 in FEC/EMC (3/7 wt %)—Control, (thick solid line) 1.2M LiPF6 in FEC/EMC (3/7 wt %)+2 wt % DTBTC+1 wt % LiDFOB, in accordance with an example embodiment of the disclosure.
Figure 9B:
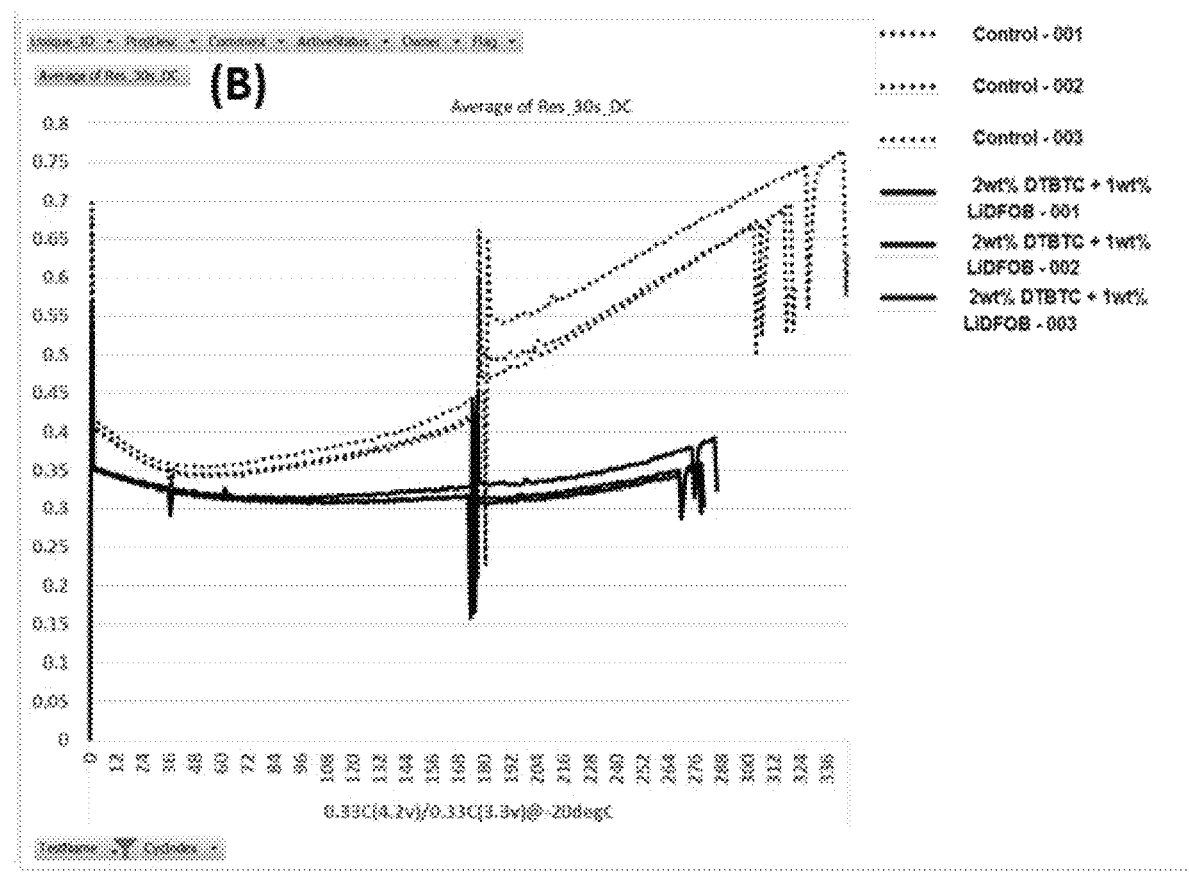

FIG. 9. Average resistance during 30s pulses for the charge (FIG. 9A) and discharge (FIG. 9B) processes of Si-dominant anode//NCA cathode full cells tested at −20° C. The electrolytes used may be: (dotted line) 1.2 M $LiPF_6$ in FEC/EMC (3/7 wt %)—Control, (thick solid line) 1.2M $LiPF_6$ in FEC/EMC (3/7 wt %)+2 wt % DTBTC+1 wt % LiDFOB. The testing temperature is −20° C.

The results in FIG. 9 show that 2 wt % DTBTC+1 wt % LiDFOB-containing cells have lower resistance increase than reference electrolyte-based control cells with the increase of cycling.

Example 3

Figure 10A:
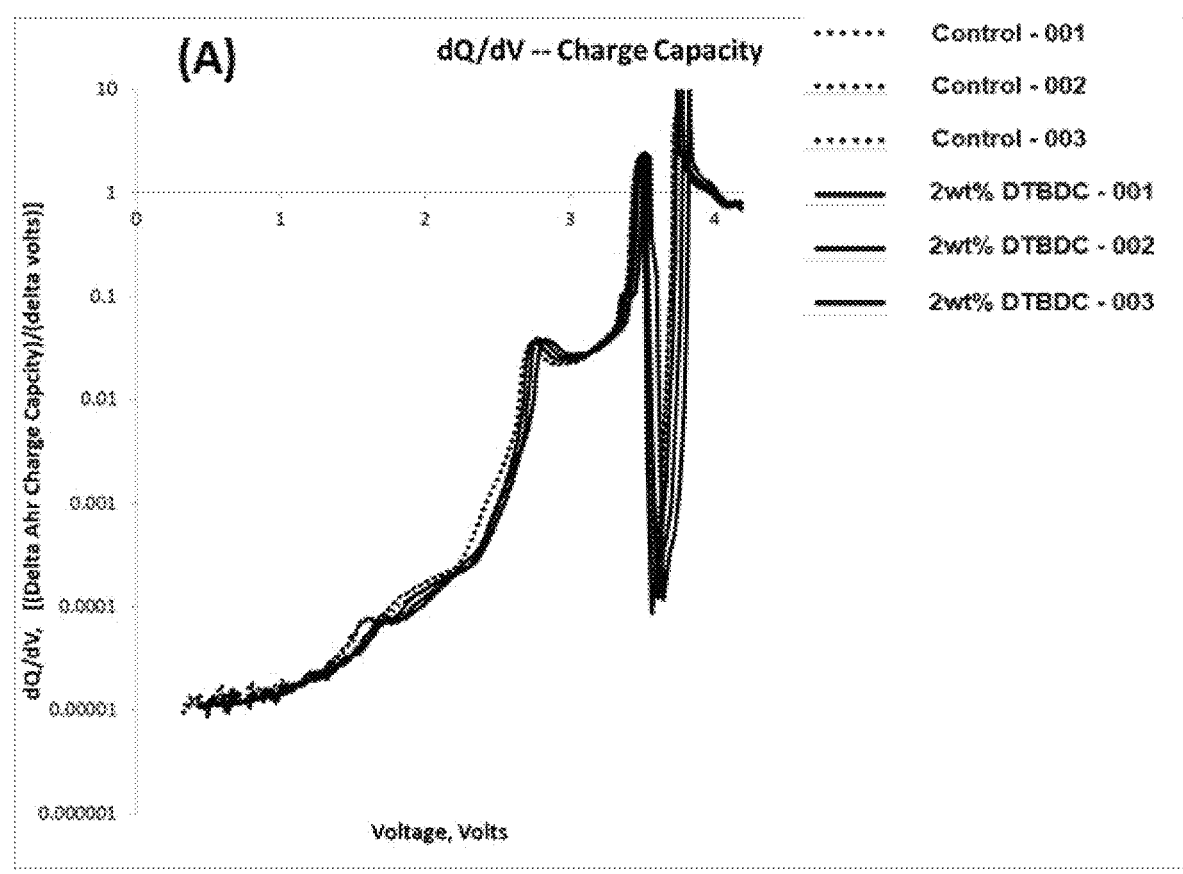
FIGS. 10A and 10B show dQ/dV curve—During Charge (FIG. 10A) and dQ/dV curve—During Discharge (FIG. 10B) of Si-dominant anode//NCA cathode full cells tested at room temperature. The electrolytes used may be: (dotted line) 1.2 M LiPF6 in FEC/EMC (3/7 wt %)—Control, (solid line) 1.2M LiPF6 in FEC/EMC (3/7 wt %)+2 wt % DTBDC, in accordance with an example embodiment of the disclosure.
Figure 10B:
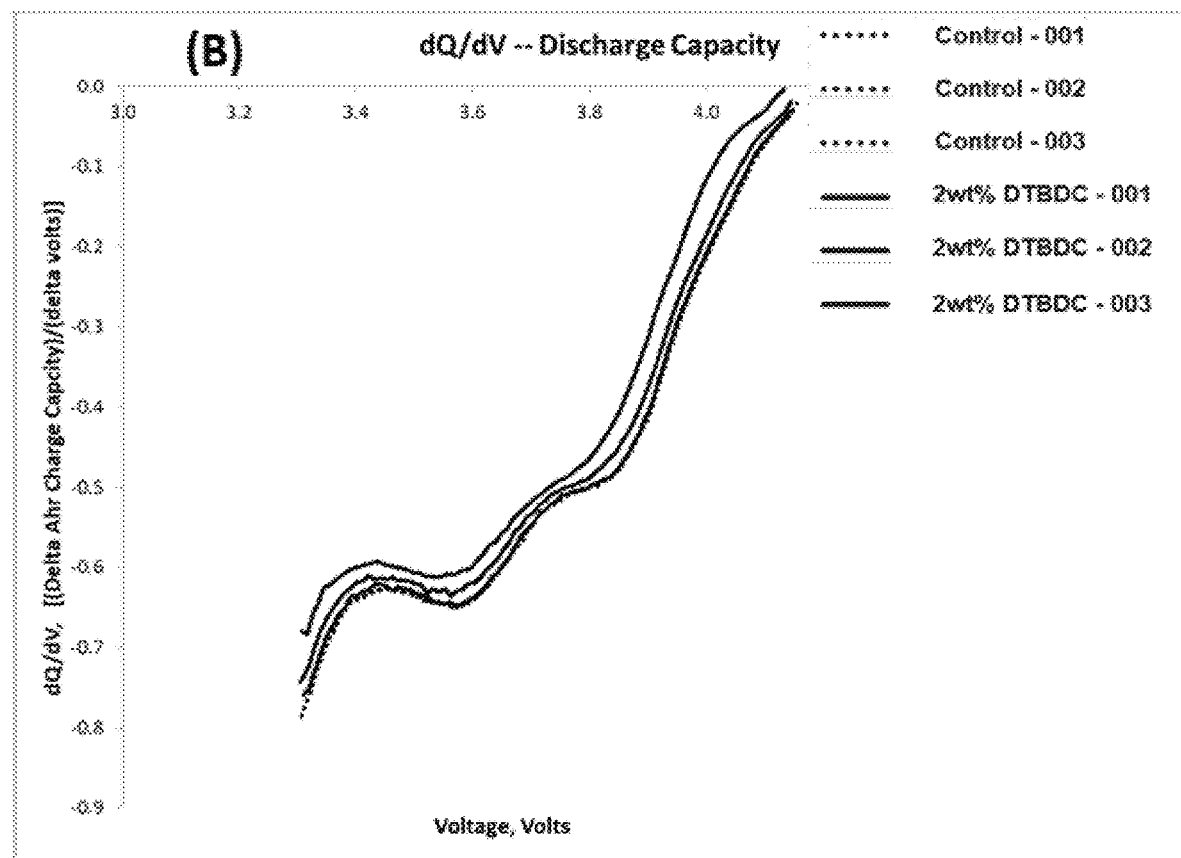

FIG. 10. dQ/dV—During Charge (FIG. 10A) and dQ/dV—During Discharge (FIG. 10B) curves of Si-dominant anode//NCA cathode full cells tested at room temperature. The electrolytes used may be: (dotted line) 1.2 M $LiPF_6$ in FEC/EMC (3/7 wt %)—Control, (solid line) 1.2M $LiPF_6$ in FEC/EMC (3/7 wt %)+2 wt % DTBDC. The Si-dominant anodes contain about 80 wt % Si, 5 wt % graphite and 15 wt % glassy carbon (from resin), and may be laminated on 15 μm Cu foil. The average loading is about 2-5 mg/cm². The cathodes contain about 92 wt % NCA, 4 wt % Super P and 4 wt % PVDF5130, and may be coated on 15 μm Al foil. The average loading is about 20-30 mg/cm².

The dQ/dV data for both control and 2 wt % DTBDC-containing cells may be obtained through the same testing protocol as the above mentioned in FIG. 2.

The 1$^{st}$ formation cycle dQ/dV curves in FIG. 10 show that 2 wt % DTBDC-containing cells have a different shape, relative to FIGS. 2 and 6, indicating different electrode electrolyte interfaces may be shown.

Figure 11A:
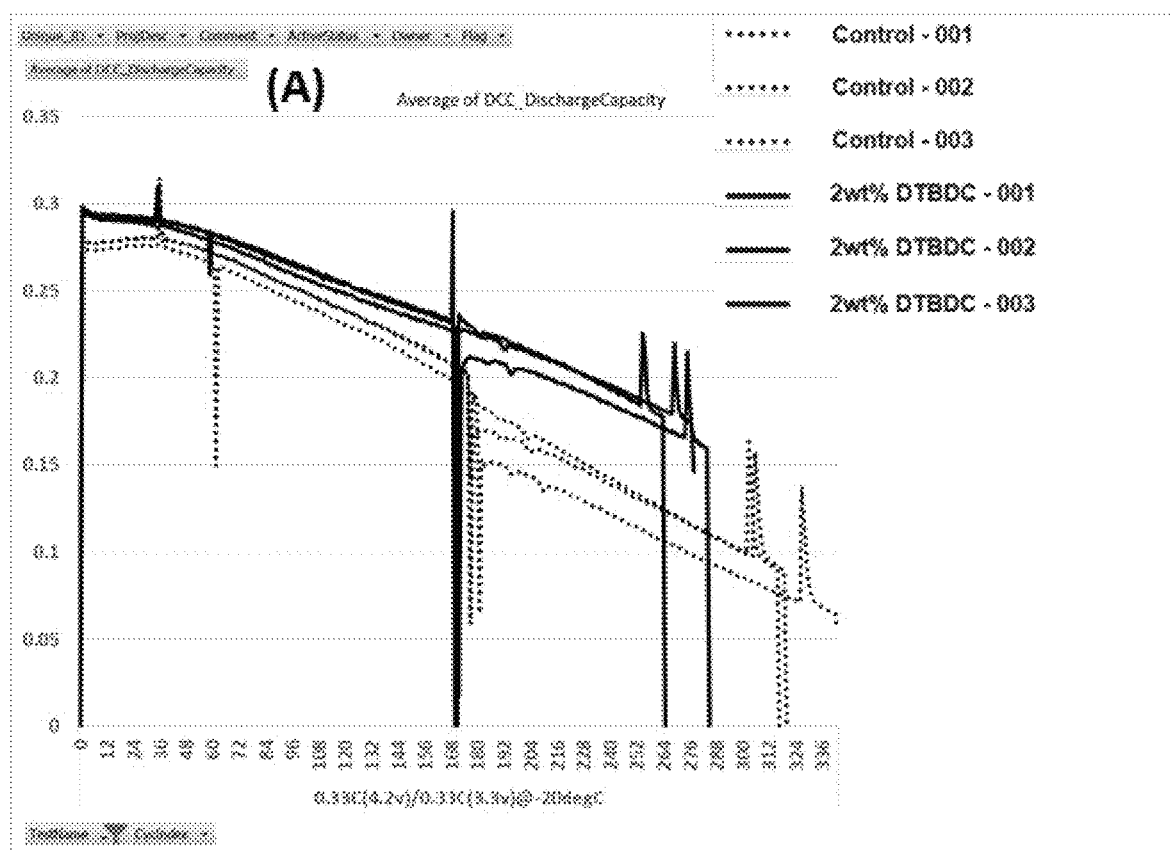
FIGS. 11A and 11B show the capacity retention (FIG. 11A) and normalized capacity retention (FIG. 11B) of Si-dominant anode//NCA cathode full cells tested at −20° C. using 2 wt % DTBDC, in accordance with an example embodiment of the disclosure.
Figure 11B:
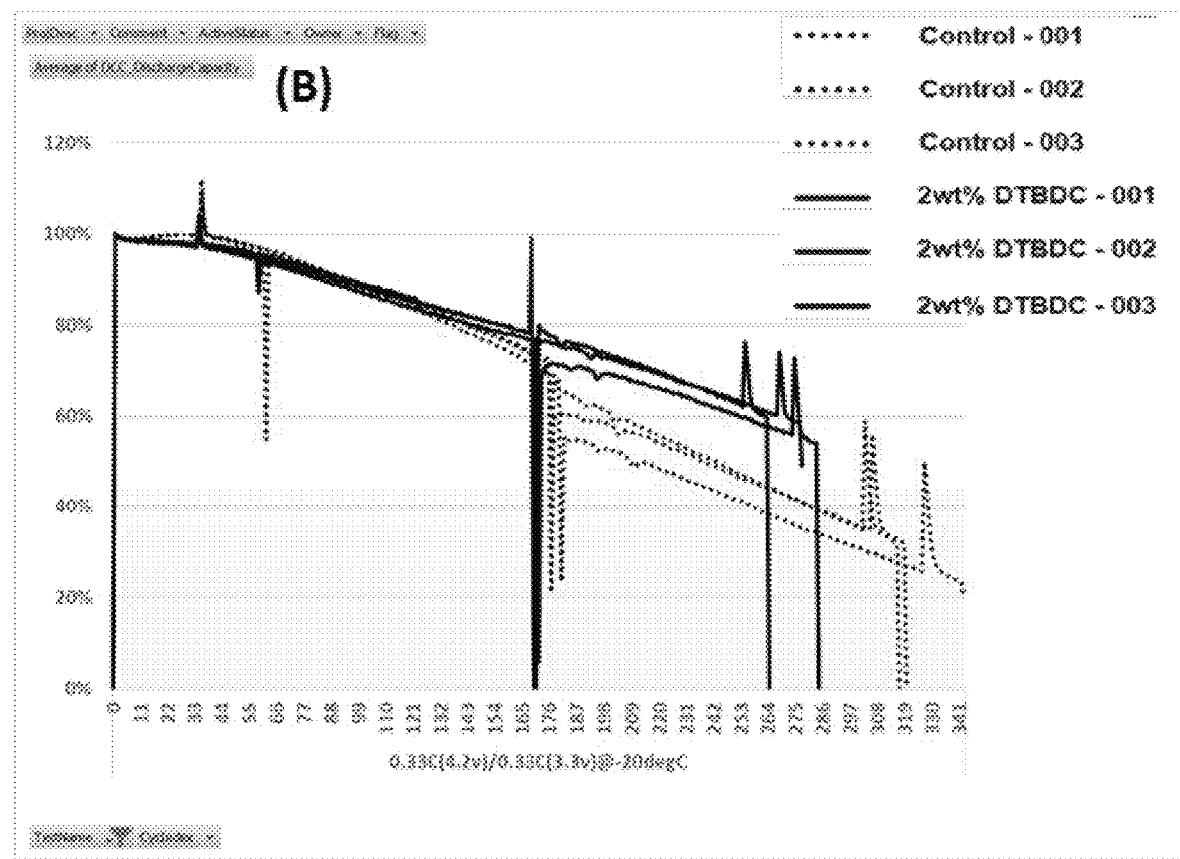

FIG. 11. Capacity retention (FIG. 11A) and Normalized capacity retention (FIG. 11B) of Si-dominant anode//NCA cathode full cells tested at −20° C. The Si-dominant anodes contain about 80 wt % Si, 5 wt % graphite and 15 wt % glassy carbon (from resin), and may be laminated on 15 μm Cu foil. The average loading is about 2-5 mg/cm². The testing temperature may be −20° C.

The long-term cycling program for both control and 2 wt % DTBDC-containing cells are the same as the above mentioned in FIG. 3.

FIG. 11 indicates that when adding 2 wt % DTBDC into 1.2 M $LiPF_6$ in FEC/EMC (3/7 wt %)-based electrolytes, the corresponding cell capacity retention is improved compared with reference electrolyte-based control cells.

Figure 12A:
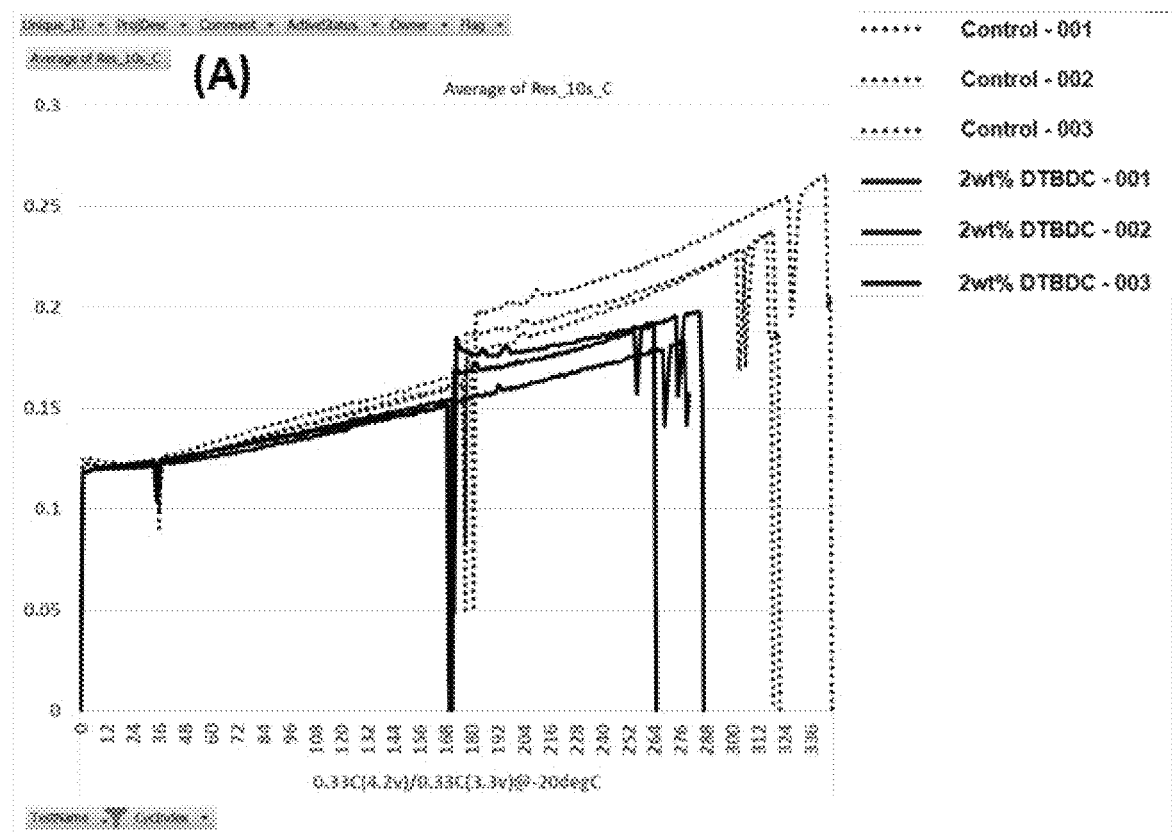
FIGS. 12A and 12B show average 10 second internal resistance for 10 s pulses during charge (FIG. 12A) and discharge (FIG. 12B) processes of Si-dominant anode//NCA cathode full cells tested at −20° C. The electrolytes used may be: (dotted line) 1.2 M LiPF6 in FEC/EMC (3/7 wt %)—Control, (thick solid line) 1.2M LiPF6 in FEC/EMC (3/7 wt %)+2 wt % DTBDC, in accordance with an example embodiment of the disclosure.
Figure 12B:
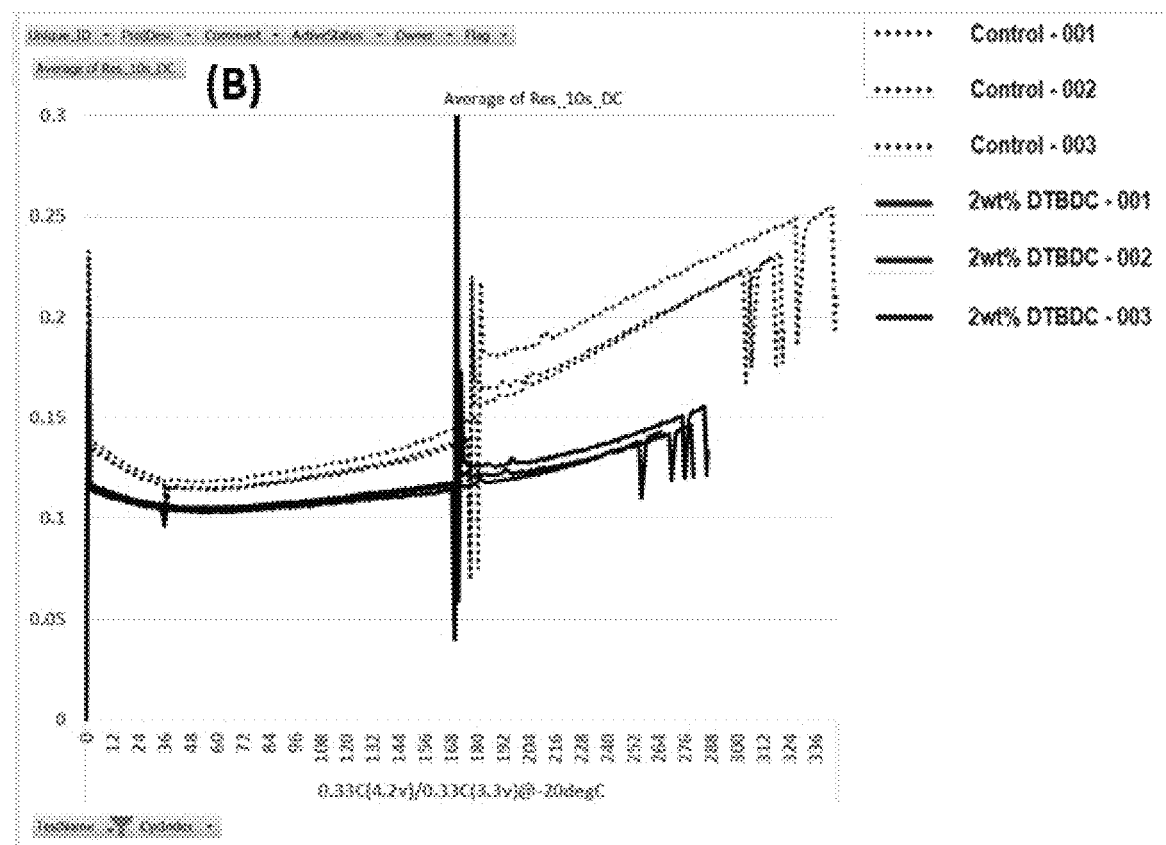

FIG. 12. Average 10 second internal resistance for 10 s pulses during charge (FIG. 12A) and discharge (FIG. 12B) processes of Si-dominant anode//NCA cathode full cells tested at −20° C. The electrolytes used may be: (dotted line) 1.2 M $LiPF_6$ in FEC/EMC (3/7 wt %)—Control, (thick solid line) 1.2M LiPF$_6$ in FEC/EMC (3/7 wt %)+2 wt % DTBDC. The testing temperature may be −20° C.

The results in FIG. 12 show that 2 wt % DTBDC-containing cells have lower resistance increase than reference electrolyte-based control cells with the increase of cycling.

Figure 13A:
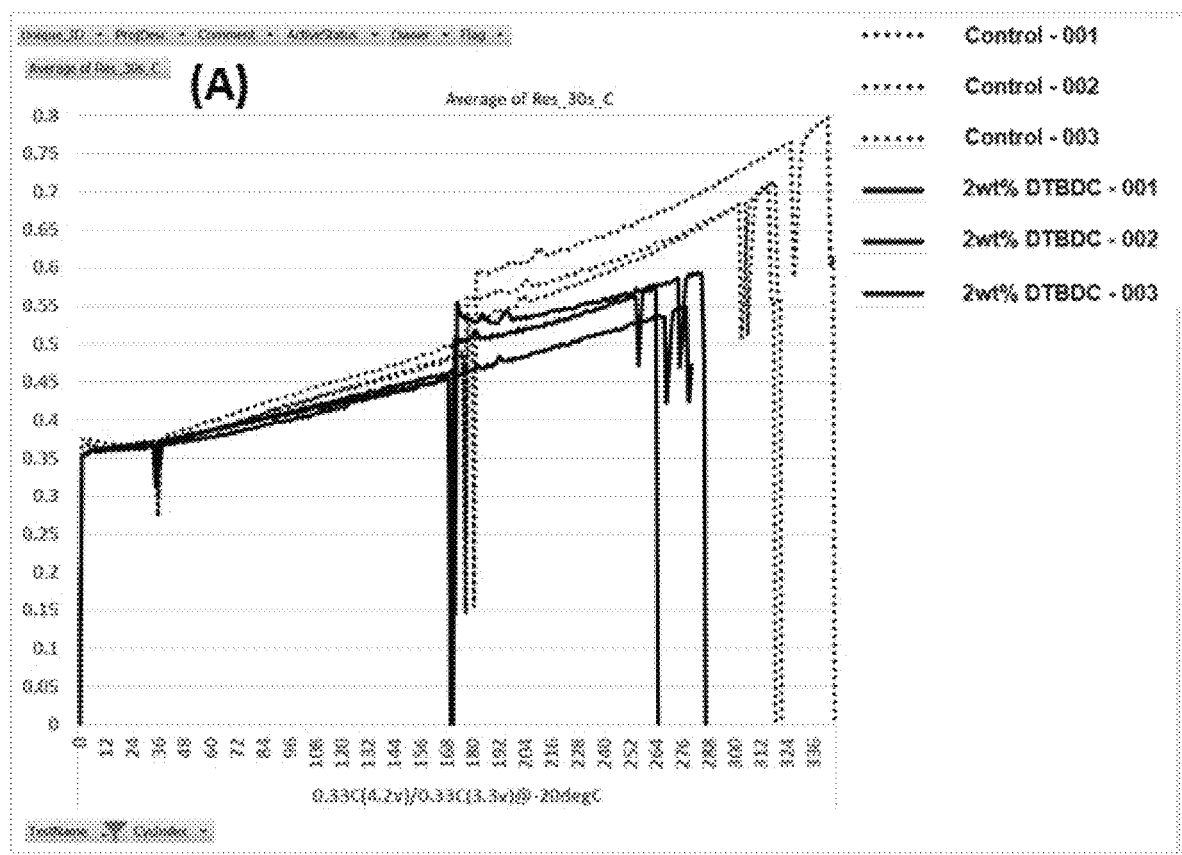
FIGS. 13A and 13B show average resistance during 30 s pulses for the charge (FIG. 13A) and discharge (FIG. 13B) processes of Si-dominant anode//NCA cathode full cells tested at −20° C. The electrolytes used may be: (dotted line) 1.2 M LiPF6 in FEC/EMC (3/7 wt %)—Control, (thick solid line) 1.2M LiPF6 in FEC/EMC (3/7 wt %)+2 wt % DTBDC, in accordance with an example embodiment of the disclosure.
Figure 13B:
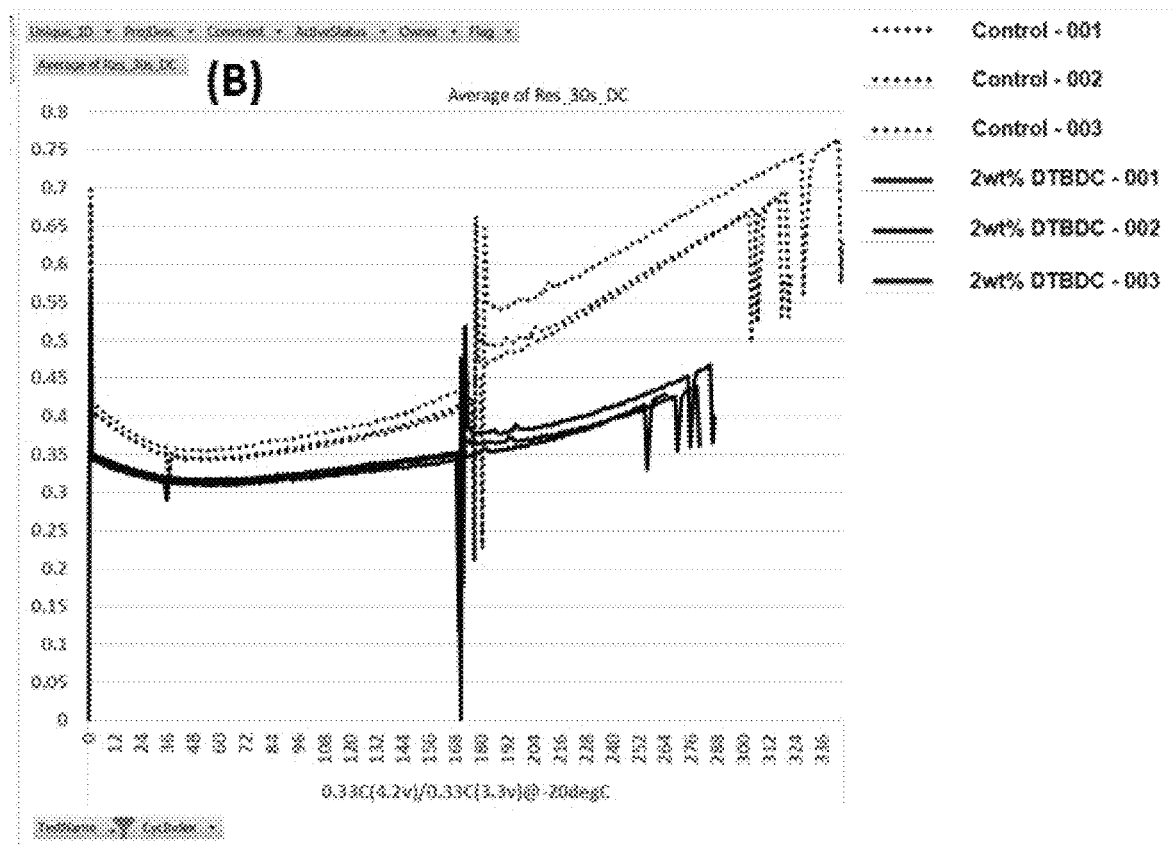

FIG. 13. Average resistance during 30s pulses for the charge (FIG. 13A) and discharge (FIG. 13B) processes of Si-dominant anode//NCA cathode full cells tested at −20° C. The electrolytes used may be: (dotted line) 1.2 M LiPF$_6$ in FEC/EMC (3/7 wt %)—Control, (thick solid line) 1.2M LiPF$_6$ in FEC/EMC (3/7 wt %)+2 wt % DTBDC. The testing temperature is −20° C.

The results in FIG. 13 show that 2 wt % DTBDC-containing cells have lower resistance increase than reference electrolyte-based control cells with the increase of cycling.

Example 4

Figure 14A:
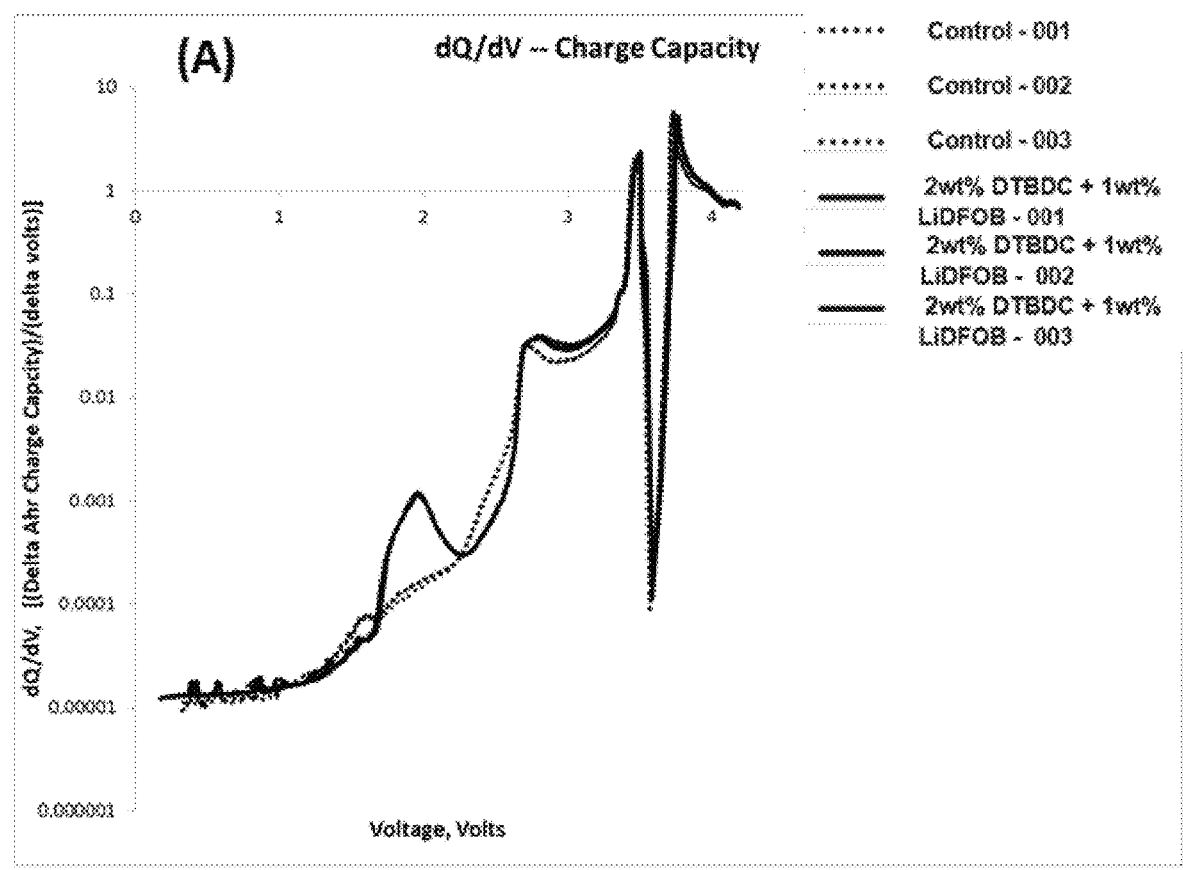
FIGS. 14A and 14B show dQ/dV curve—During Charge (FIG. 14A) and dQ/dV curve—During Discharge (FIG. 14B) of Si-dominant anode//NCA cathode full cells tested at room temperature. The electrolytes used may be: (dotted line) 1.2 M LiPF6 in FEC/EMC (3/7 wt %)—Control, (solid line) 1.2M LiPF6 in FEC/EMC (3/7 wt %)+2 wt % DTBDC+1 wt % LiDFOB, in accordance with an example embodiment of the disclosure.
Figure 14B:
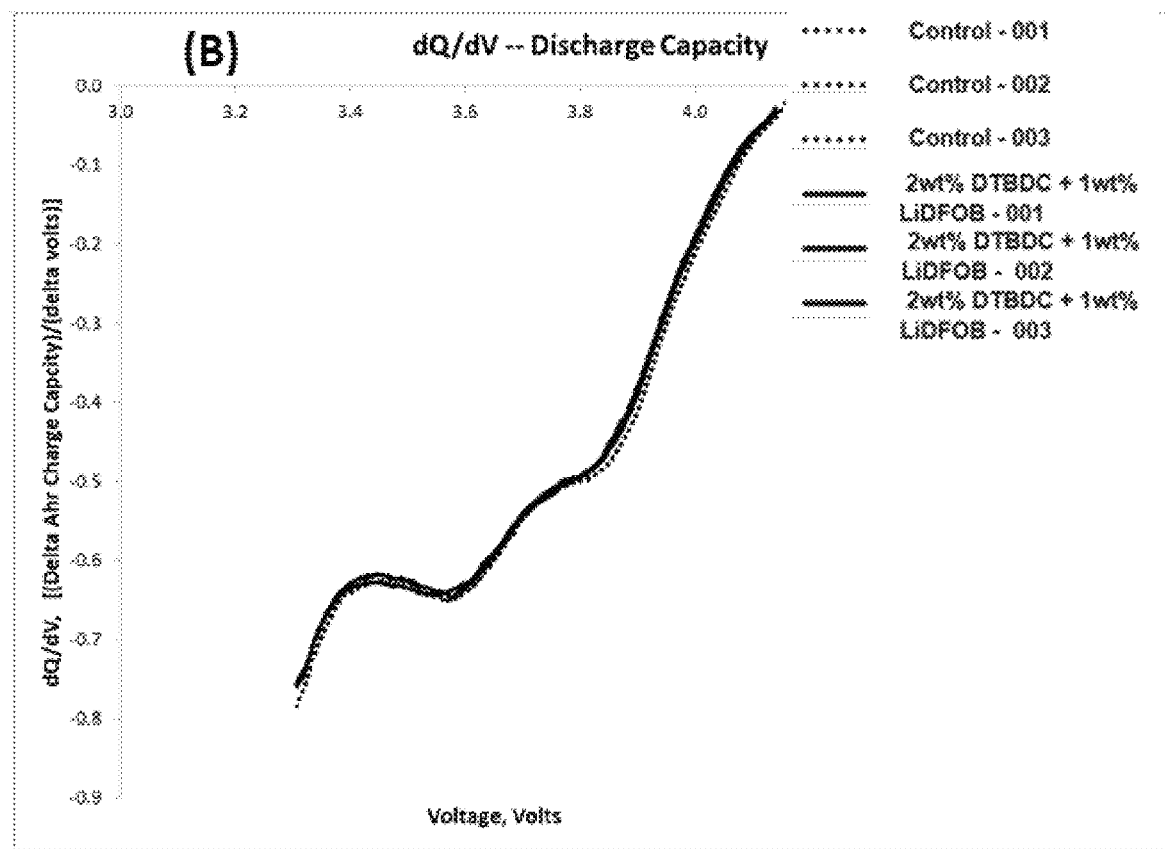

FIG. 14. dQ/dV—During Charge (FIG. 14A) and dQ/dV—During Discharge (FIG. 14B) curves of Si-dominant anode//NCA cathode full cells tested at room temperature. The electrolytes used may be: (dotted line) 1.2 M LiPF$_6$ in FEC/EMC (3/7 wt %)—Control, (solid line) 1.2M LiPF$_6$ in FEC/EMC (3/7 wt %)+2 wt % DTBDC+1 wt % LiDFOB. The Si-dominant anodes contain about 80 wt % Si, 5 wt % graphite and 15 wt % glassy carbon (from resin), and may be laminated on 15 μm Cu foil. The average loading is about 2-5 mg/cm$^2$. The cathodes contain about 92 wt % NCA, 4 wt % Super P and 4 wt % PVDF5130, and may be coated on 15 μm Al foil. The average loading is about 20-30 mg/cm$^2$.

The dQ/dV data for both control and 2 wt % DTBDC+1 wt % LiDFOB-containing cells may be obtained through the same testing protocol as the above mentioned in FIG. 2.

The 1$^{st}$ formation cycle dQ/dV curves in FIG. 14 show that 2 wt % DTBDC+1 wt % LiDFOB-containing cells have a strong peak at around 2V which indicates a significantly different SEI layer being formed, relative to FIGS. 2, 6 and 10, due to the presence of LiDFOB salt in the electrolyte formulation.

Figure 15A:
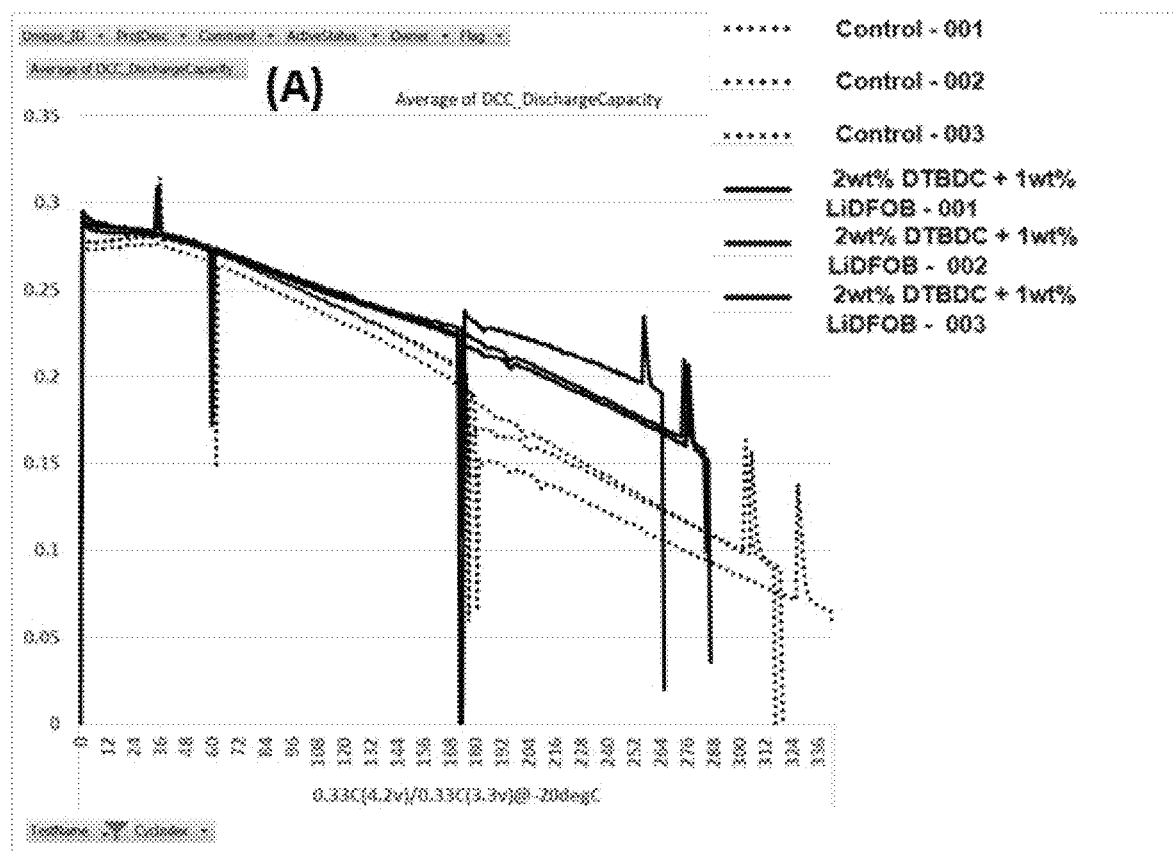
FIGS. 15A and 15B show the capacity retention (FIG. 15A) and normalized capacity retention (FIG. 15B) of Si-dominant anode//NCA cathode full cells tested at −20° C. using 2 wt % DTBDC+1 wt % LiDFOB, in accordance with an example embodiment of the disclosure.
Figure 15B:
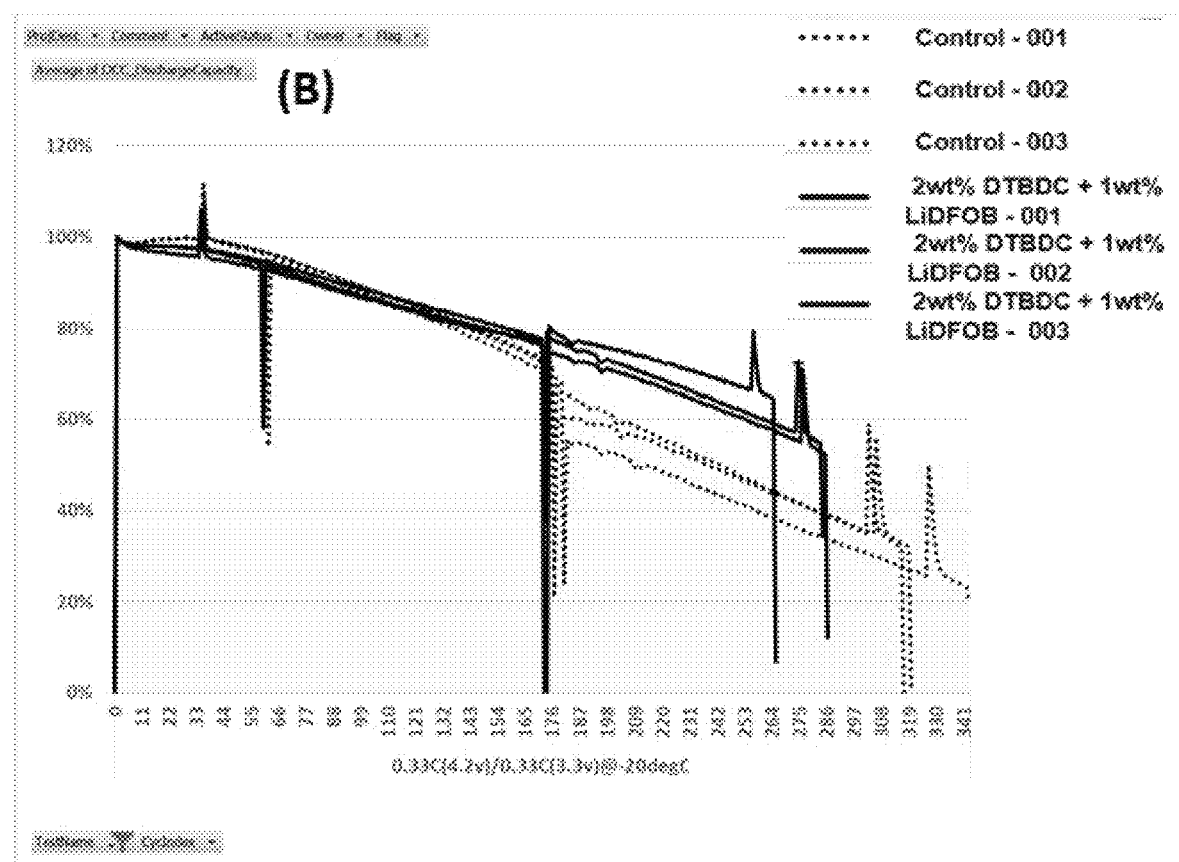

FIG. 15. Capacity retention (FIG. 15A) and Normalized capacity retention (FIG. 15B) of Si-dominant anode//NCA cathode full cells tested at −20° C. The Si-dominant anodes contain about 80 wt % Si, 5 wt % graphite and 15 wt % glassy carbon (from resin), and may be laminated on 15 μm Cu foil. The average loading is about 2-5 mg/cm$^2$. The testing temperature may be −20° C.

The long-term cycling program for both control and 2 wt % DTBDC+1 wt % LiDFOB-containing cells are the same as the above mentioned in FIG. 3.

FIG. 15 indicates that when adding 2 wt % DTBDC+1 wt % LiDFOB into 1.2 M LiPF$_6$ in FEC/EMC (3/7 wt %)-based electrolytes, the corresponding cell capacity retention is improved compared with reference electrolyte-based control cells.

Figure 16A:
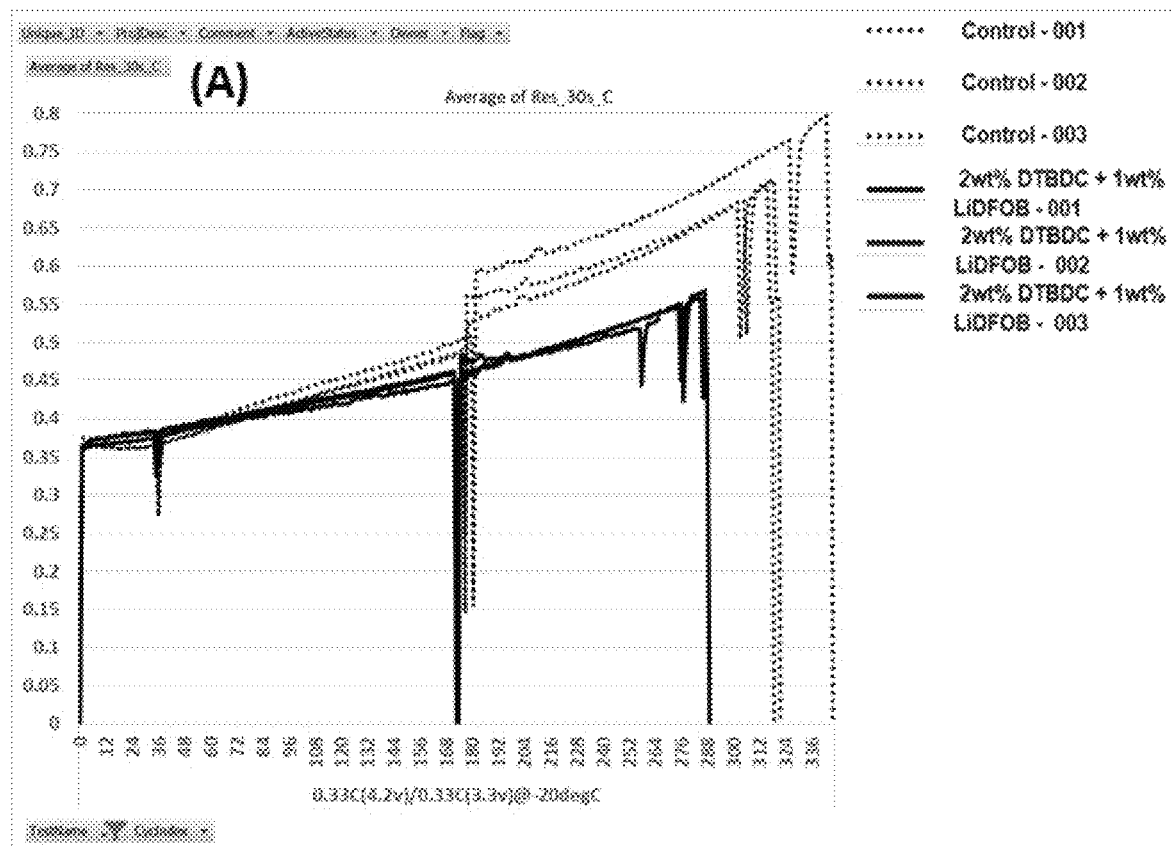
FIGS. 16A and 16B show average 30 second internal resistance for 30 s pulses during charge (FIG. 16A) and discharge (FIG. 16B) processes of Si-dominant anode//NCA cathode full cells tested at −20° C. The electrolytes used may be: (dotted line) 1.2 M LiPF6 in FEC/EMC (3/7 wt %)—Control, (thick solid line) 1.2M LiPF6 in FEC/EMC (3/7 wt %)+2 wt % DTBDC+1 wt % LiDFOB, in accordance with an example embodiment of the disclosure.
Figure 16B:
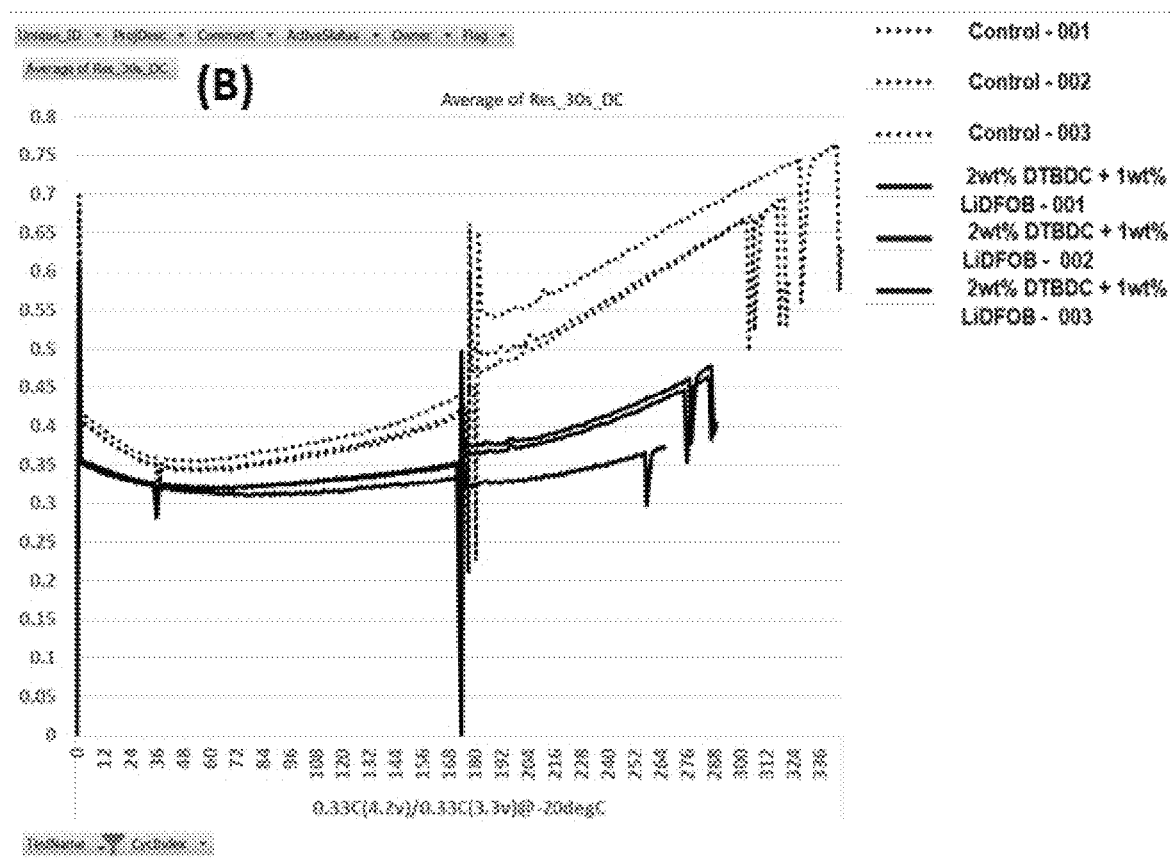

FIG. 16. Average 30 second internal resistance for 30s pulses during charge (FIG. 16A) and discharge (FIG. 16B) processes of Si-dominant anode//NCA cathode full cells tested at −20° C. The electrolytes used may be: (dotted line) 1.2 M LiPF$_6$ in FEC/EMC (3/7 wt %)—Control, (thick solid line) 1.2M LiPF$_6$ in FEC/EMC (3/7 wt %)+2 wt % DTBDC+1 wt % LiDFOB. The testing temperature may be −20° C.

The results in FIG. 16 show that 2 wt % DTBDC+1 wt % LiDFOB-containing cells have lower resistance increase than reference electrolyte-based control cells with the increase of cycling.

Various embodiments have been described above. Although the invention has been described with reference to these specific embodiments, the descriptions are intended to be illustrative and are not intended to be limiting. Various modifications and applications may occur to those skilled in the art without departing from the true spirit and scope of the invention as defined in the appended claims.

What is claimed is:
1. An energy storage device comprising:
   a first electrode and a second electrode, where one or both of the first electrode and the second electrode is a Si-based electrode;
   a separator between the first electrode and the second electrode;
   an electrolyte; and
   at least one electrolyte additive compound comprising a trioxidane, peroxoate, dioxetanone, oxepane dione, oxetane dione or 1,4-dioxane-2,3-dione; each of which is optionally substituted.
2. The energy storage device of claim 1, wherein the second electrode is a Si-dominant electrode.
3. The energy storage device of claim 1, wherein the second electrode comprises a self-supporting composite material film.
4. The energy storage device of claim 3, wherein the composite material film comprises:
   greater than 0% and less than 90% by weight of silicon particles, and
   greater than 0% and less than 90% by weight of one or more types of carbon phases, wherein at least one of the one or more types of carbon phases is a substantially continuous phase that holds the composite material film together such that the silicon particles are distributed throughout the composite material film.
5. The energy storage device of claim 1, wherein the electrolyte further comprises fluoroethylene carbonate (FEC).
6. The energy storage device of claim 5, wherein the electrolyte is substantially free of non-fluorine containing cyclic carbonate.
7. The energy storage device of claim 1, wherein the electrolyte additive compound is selected from the group consisting of formulae (D), (H), (I), (L), (M), (O) and (Q):

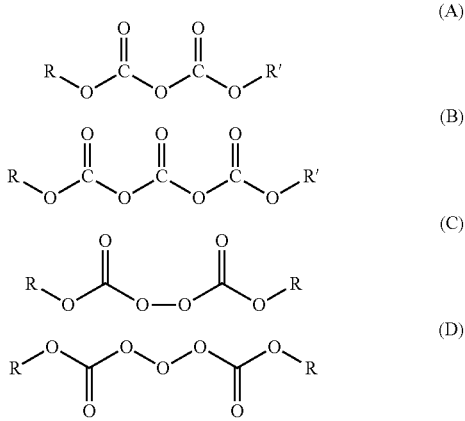

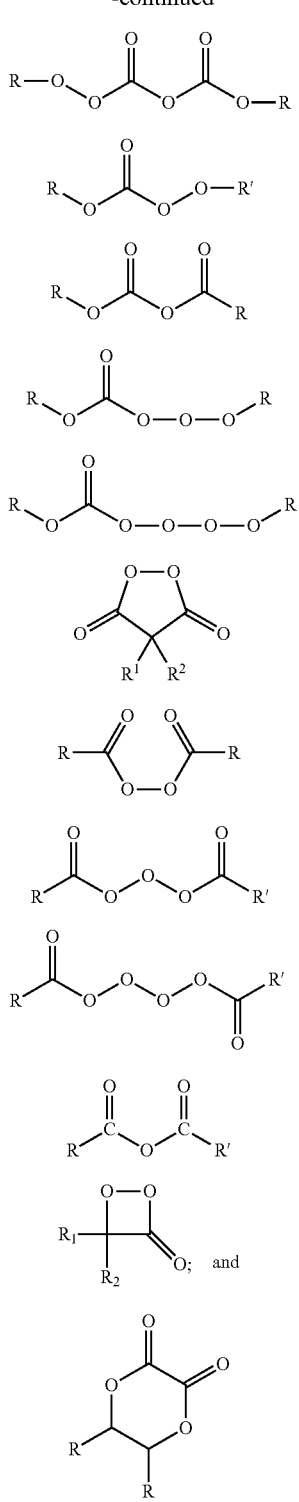

wherein each individual R, R', R¹ or R² group are the same or different and are selected from —H, —CN, an alkenyl, a heteroalkenyl, an alkynyl, a heteroalkynyl, an alkyl, —Si(CH³)₃, a cycloalkyl and a heterocycloalkyl; each of which is optionally substituted by —F, —CN, —CF₃ or a heterocycloalkyl.

8. The energy storage device of claim 1, wherein the electrolyte additive compound is selected from the group consisting of 2-ethylhexyl 3-tert-butyltrioxidane-1-carboxylate; acetyl butaneperoxoate (CAS: 13043-83-9); propanoyl butaneperoxoate (CAS: 13043-86-2); (2,2,2-trifluoroacetyl) oxy 2,2,2-trifluoroethaneperoxoate; (2,2,2-trifluoroacetyl) peroxy 2,2,2-trifluoroethaneperoxoate (CAS: 684-80-0); 1,2,3,4,6-pentaoxepane-5,7-dione; 1,2-Dioxetane-3,4-dione (CAS: 26974-08-3); 3,3-dimethyl-1,2-dioxetanone; 3-tert-butyl-1,2-dioxetanone; spiro-cyclopentyl-1,2-dioxetanone; spiro-adamantyl-1,2-dioxetanone; firefly dioxetanone; 1,4-dioxane-2,3-dione; 5-methylidene-1,4-dioxane-2,3-dione; 5-ethenyl-1,4-dioxane-2,3-dione (CAS: 89543-86-2); 5-methyl-1,4-dioxane-2,3-dione (CAS: 89093-66-3); 5,6-dimethyl-1,4-dioxane-2,3-dione (CAS: 89093-67-4); and cis-5,6-diphenyl-1,4-dioxane-2,3-dione (CAS: 74888-53-2).

9. A method of forming an energy storage device, the method comprising:
forming an energy storage device comprising a cathode, an electrolyte, and an anode, wherein said anode is a Si-based electrode; and
wherein said one or both of said cathode and said anode contain one or more electrolyte additive compounds, wherein said one or more electrolyte additive compounds is selected from the group consisting of trioxidane, peroxoate, dioxetanone, oxepane dione, oxetane dione and 1,4-dioxane-2,3-dione; each of which is optionally substituted;
wherein said one or both of said cathode and said anode is formed using, at least, the following steps:
an electrode material is mixed to create a slurry;
said one or more electrolyte additive compounds is added to said slurry;
said slurry is coated on metal foil; and
the coated metal foil is dried.

10. The method of claim 9, wherein the second electrode is a Si-dominant electrode.

11. The method of claim 9, wherein the second electrode comprises a self-supporting composite material film.

12. The method of claim 11, wherein the composite material film comprises:
greater than 0% and less than 90% by weight of silicon particles, and
greater than 0% and less than 90% by weight of one or more types of carbon phases, wherein at least one of the one or more types of carbon phases is a substantially continuous phase that holds the composite material film together such that the silicon particles are distributed throughout the composite material film.

13. The method of claim 9, wherein the electrolyte further comprises fluoroethylene carbonate (FEC).

14. The method of claim 13, wherein the electrolyte is substantially free of non-fluorine containing cyclic carbonate.

15. The method of claim 9, wherein the electrolyte additive compound is selected from the group consisting of formulae (D), (H), (D), (L), (M), (O) and (Q):

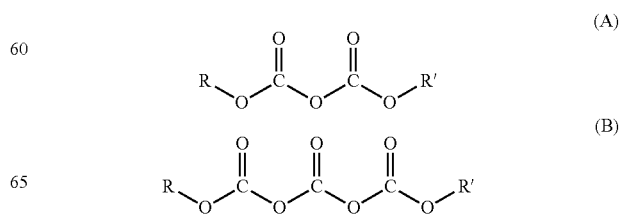

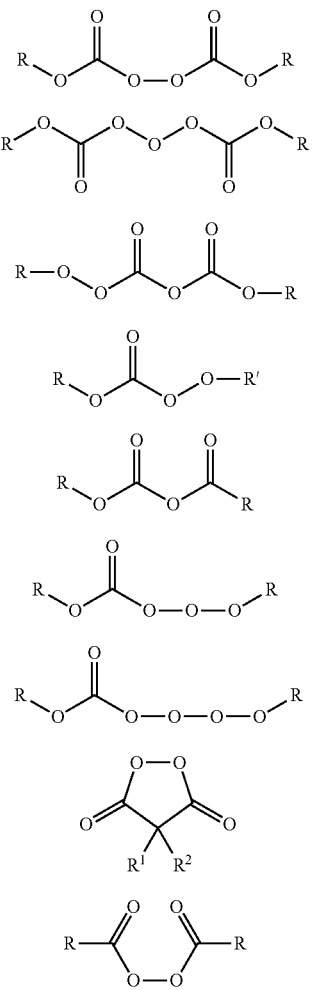
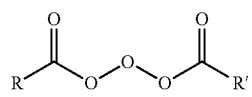
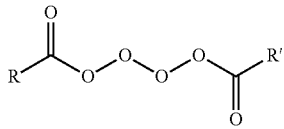
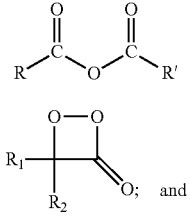
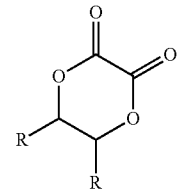
wherein each individual R, R', $R^1$ or $R^2$ group are the same or different and are selected from —H, —CN, an alkenyl, a heteroalkenyl, an alkynyl, a heteroalkynyl, an alkyl, —Si$(CH^3)_3$, a cycloalkyl and a heterocycloalkyl; each of which is optionally substituted by —F, —CN, —$CF_3$ or a heterocycloalkyl.
* * * * *